(12) United States Patent
Jafari et al.

(10) Patent No.: US 8,448,641 B2
(45) Date of Patent: *May 28, 2013

(54) LEAK-COMPENSATED PROPORTIONAL ASSIST VENTILATION

(75) Inventors: Mehdi M. Jafari, Laguna Hills, CA (US); Rhomere S. Jimenez, Winchester, CA (US); Gail F. Upham, Fallbrook, CA (US); Jeffrey K. Aviano, Escondido, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/565,595

(22) Filed: Aug. 2, 2012

(65) Prior Publication Data

US 2012/0304997 A1 Dec. 6, 2012

Related U.S. Application Data

(62) Division of application No. 12/408,408, filed on Mar. 20, 2009, now Pat. No. 8,267,085.

(51) Int. Cl.
*F16K 31/02* (2006.01)

(52) U.S. Cl.
USPC ............ 128/204.21; 128/200.24; 128/202.22; 128/204.18; 128/204.23; 128/204.22

(58) Field of Classification Search
USPC ............. 128/200.24, 204.18, 204.21–204.23
See application file for complete search history.

(56) References Cited

U.S. PATENT DOCUMENTS

| 3,805,780 A | 4/1974 | Cramer et al. |
| 3,941,124 A | 3/1976 | Rodewald et al. |
| 4,056,098 A | 11/1977 | Michel et al. |
| 4,305,388 A | 12/1981 | Brisson |
| 4,340,044 A | 7/1982 | Levy et al. |
| 4,448,192 A | 5/1984 | Stawitcke et al. |
| 4,752,089 A | 6/1988 | Carter |
| 4,766,894 A | 8/1988 | Legrand et al. |
| 4,921,642 A | 5/1990 | LaTorraca |
| 4,939,647 A | 7/1990 | Clough et al. |
| 4,954,799 A | 9/1990 | Kumar |
| 4,971,052 A | 11/1990 | Edwards |

(Continued)

FOREIGN PATENT DOCUMENTS

| DE | 19808543 A1 | 11/1998 |
| EP | 0425092 A | 5/1991 |

(Continued)

OTHER PUBLICATIONS

PCT International Search Report and Written Opinion in Application PCT/2009/038810, mailed Jul. 6, 2009, 16 pgs.

(Continued)

*Primary Examiner* — Lynne Anderson
*Assistant Examiner* — Bradley Philips

(57) ABSTRACT

This disclosure describes systems and methods for compensating for leakage when during delivery of gas from a medical ventilator in a proportional assist mode to a patient. The technology described herein includes systems and methods to compensate the delivery of PA ventilation for leakage in the patient circuit by using leak-compensated lung flows as well as leak-compensated respiratory mechanics parameters (lung compliance and lung resistance) estimated in a manner that compensates for elastic and inelastic leaks from the ventilation system.

7 Claims, 6 Drawing Sheets

U.S. PATENT DOCUMENTS

| | | |
|---|---|---|
| 4,972,842 A | 11/1990 | Korten et al. |
| 4,986,268 A | 1/1991 | Tehrani |
| 5,057,822 A | 10/1991 | Hoffman |
| 5,072,728 A | 12/1991 | Pasternack |
| 5,072,737 A | 12/1991 | Goulding |
| 5,094,235 A | 3/1992 | Westenskow et al. |
| 5,148,802 A | 9/1992 | Sanders et al. |
| 5,150,291 A | 9/1992 | Cummings et al. |
| 5,161,525 A | 11/1992 | Kimm et al. |
| 5,237,987 A | 8/1993 | Anderson et al. |
| 5,239,995 A | 8/1993 | Estes et al. |
| 5,259,373 A | 11/1993 | Gruenke et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,313,937 A | 5/1994 | Zdrojkowski et al. |
| 5,315,989 A | 5/1994 | Tobia |
| 5,316,009 A | 5/1994 | Yamada |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,365,922 A | 11/1994 | Raemer |
| 5,368,019 A | 11/1994 | LaTorraca |
| 5,383,449 A | 1/1995 | Forare et al. |
| 5,385,142 A | 1/1995 | Brady et al. |
| 5,388,575 A | 2/1995 | Taube |
| 5,390,666 A | 2/1995 | Kimm et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,429,123 A | 7/1995 | Shaffer et al. |
| 5,433,193 A | 7/1995 | Sanders et al. |
| 5,438,980 A | 8/1995 | Phillips |
| 5,443,075 A | 8/1995 | Holscher |
| 5,492,113 A | 2/1996 | Estes et al. |
| 5,503,146 A | 4/1996 | Froehlich et al. |
| 5,503,147 A | 4/1996 | Bertheau |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,540,220 A | 7/1996 | Gropper et al. |
| 5,542,415 A | 8/1996 | Brady |
| 5,544,674 A | 8/1996 | Kelly |
| 5,549,106 A | 8/1996 | Gruenke et al. |
| 5,551,418 A | 9/1996 | Estes et al. |
| 5,551,419 A | 9/1996 | Froehlich et al. |
| 5,555,880 A | 9/1996 | Winter et al. |
| 5,596,984 A | 1/1997 | O'Mahoney et al. |
| 5,598,838 A | 2/1997 | Servidio et al. |
| 5,605,151 A | 2/1997 | Lynn |
| 5,623,923 A | 4/1997 | Bertheau et al. |
| 5,630,411 A | 5/1997 | Holscher |
| 5,632,269 A | 5/1997 | Zdrojkowski |
| 5,632,270 A | 5/1997 | O'Mahoney et al. |
| 5,645,048 A | 7/1997 | Brodsky et al. |
| 5,645,053 A | 7/1997 | Remmers et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,685,296 A | 11/1997 | Zdrojkowski et al. |
| 5,687,715 A | 11/1997 | Landis et al. |
| 5,692,497 A | 12/1997 | Schnitzer et al. |
| 5,715,812 A | 2/1998 | Deighan et al. |
| 5,752,509 A | 5/1998 | Lachmann et al. |
| 5,762,480 A | 6/1998 | Adahan |
| 5,771,884 A | 6/1998 | Yarnall et al. |
| 5,791,339 A | 8/1998 | Winter |
| 5,794,615 A | 8/1998 | Estes |
| 5,794,986 A | 8/1998 | Gansel et al. |
| 5,803,065 A | 9/1998 | Zdrojkowski et al. |
| 5,813,399 A | 9/1998 | Isaza et al. |
| 5,823,187 A | 10/1998 | Estes et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,876,352 A | 3/1999 | Weismann |
| 5,881,717 A | 3/1999 | Isaza |
| 5,881,723 A | 3/1999 | Wallace et al. |
| 5,884,622 A | 3/1999 | Younes |
| 5,884,623 A | 3/1999 | Winter |
| 5,891,023 A | 4/1999 | Lynn |
| 5,901,704 A | 5/1999 | Estes et al. |
| 5,904,141 A | 5/1999 | Estes et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,927,274 A | 7/1999 | Servidio et al. |
| 5,934,274 A | 8/1999 | Merrick et al. |
| 5,970,975 A | 10/1999 | Estes et al. |
| 6,024,089 A | 2/2000 | Wallace et al. |
| 6,029,664 A | 2/2000 | Zdrojkowski et al. |
| 6,041,780 A | 3/2000 | Richard et al. |
| 6,047,860 A | 4/2000 | Sanders |
| 6,055,981 A | 5/2000 | Laswick et al. |
| 6,076,523 A | 6/2000 | Jones et al. |
| 6,105,575 A | 8/2000 | Estes et al. |
| 6,116,240 A | 9/2000 | Merrick et al. |
| 6,116,464 A | 9/2000 | Sanders |
| 6,123,073 A | 9/2000 | Schlawin et al. |
| 6,123,074 A | 9/2000 | Hete et al. |
| 6,135,106 A | 10/2000 | Dirks et al. |
| 6,142,150 A | 11/2000 | O'Mahony |
| 6,148,814 A | 11/2000 | Clemmer et al. |
| 6,152,129 A | 11/2000 | Berthon-Jones |
| 6,158,432 A | 12/2000 | Biondi et al. |
| 6,161,539 A | 12/2000 | Winter |
| 6,220,245 B1 | 4/2001 | Takabayashi et al. |
| 6,223,064 B1 | 4/2001 | Lynn et al. |
| 6,253,765 B1 | 7/2001 | Högnelid et al. |
| 6,257,234 B1 * | 7/2001 | Sun .................... 128/204.18 |
| 6,269,812 B1 | 8/2001 | Wallace et al. |
| 6,273,444 B1 | 8/2001 | Power |
| 6,279,569 B1 | 8/2001 | Berthon-Jones |
| 6,283,119 B1 | 9/2001 | Bourdon |
| 6,286,508 B1 | 9/2001 | Remmers et al. |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,321,748 B1 | 11/2001 | O'Mahoney |
| 6,325,785 B1 | 12/2001 | Babkes et al. |
| 6,342,039 B1 | 1/2002 | Lynn et al. |
| 6,357,438 B1 | 3/2002 | Hansen |
| 6,360,741 B2 | 3/2002 | Truschel |
| 6,360,745 B1 | 3/2002 | Wallace et al. |
| 6,369,838 B1 | 4/2002 | Wallace et al. |
| 6,371,114 B1 | 4/2002 | Schmidt et al. |
| 6,390,091 B1 | 5/2002 | Banner et al. |
| 6,412,483 B1 | 7/2002 | Jones et al. |
| 6,425,395 B1 | 7/2002 | Brewer et al. |
| 6,427,689 B1 | 8/2002 | Estes et al. |
| 6,439,229 B1 | 8/2002 | Du et al. |
| 6,467,478 B1 | 10/2002 | Merrick et al. |
| 6,484,719 B1 | 11/2002 | Berthon-Jones |
| 6,512,938 B2 | 1/2003 | Claure et al. |
| 6,532,957 B2 | 3/2003 | Berthon-Jones |
| 6,532,958 B1 | 3/2003 | Buan et al. |
| 6,532,959 B1 | 3/2003 | Berthon-Jones |
| 6,532,960 B1 | 3/2003 | Yurko |
| 6,536,429 B1 | 3/2003 | Pavlov et al. |

| Patent | Date | Inventor |
|---|---|---|
| 6,536,432 B2 | 3/2003 | Truschel |
| 6,539,940 B2 | 4/2003 | Zdrojkowski et al. |
| 6,543,449 B1 | 4/2003 | Woodring et al. |
| 6,546,930 B1 | 4/2003 | Emerson et al. |
| 6,550,478 B2 | 4/2003 | Remmers et al. |
| 6,553,991 B1 | 4/2003 | Isaza |
| 6,553,992 B1 | 4/2003 | Berthon-Jones et al. |
| 6,557,553 B1 | 5/2003 | Borrello |
| 6,561,187 B2 | 5/2003 | Schmidt et al. |
| 6,571,795 B2 | 6/2003 | Bourdon |
| 6,575,163 B1 | 6/2003 | Berthon-Jones |
| 6,578,575 B1 | 6/2003 | Jonson |
| 6,609,016 B1 | 8/2003 | Lynn |
| 6,609,517 B1 | 8/2003 | Estes et al. |
| 6,615,834 B2 | 9/2003 | Gradon et al. |
| 6,622,726 B1 | 9/2003 | Du |
| 6,626,175 B2 | 9/2003 | Jafari et al. |
| 6,629,527 B1 | 10/2003 | Estes et al. |
| 6,640,806 B2 | 11/2003 | Yurko |
| 6,644,310 B1 | 11/2003 | Delache et al. |
| 6,644,312 B2 | 11/2003 | Berthon-Jones et al. |
| 6,644,316 B2 | 11/2003 | Bowman et al. |
| 6,659,101 B2 | 12/2003 | Berthon-Jones |
| 6,668,824 B1 | 12/2003 | Isaza et al. |
| 6,671,529 B2 | 12/2003 | Claure et al. |
| 6,675,801 B2 | 1/2004 | Wallace et al. |
| 6,688,307 B2 | 2/2004 | Berthon-Jones |
| 6,701,926 B2 | 3/2004 | Olsen et al. |
| 6,718,974 B1 | 4/2004 | Moberg |
| 6,722,365 B2 | 4/2004 | Nilsson et al. |
| 6,723,055 B2 | 4/2004 | Hoffman |
| 6,723,132 B2 | 4/2004 | Salehpoor |
| 6,725,447 B1 | 4/2004 | Gilman et al. |
| 6,739,337 B2 | 5/2004 | Isaza |
| 6,748,252 B2 | 6/2004 | Lynn et al. |
| 6,752,150 B1 | 6/2004 | Remmers et al. |
| 6,752,151 B2 | 6/2004 | Hill |
| 6,755,193 B2 | 6/2004 | Berthon-Jones et al. |
| 6,758,216 B1 | 7/2004 | Berthon-Jones et al. |
| 6,760,608 B2 | 7/2004 | Lynn |
| 6,761,165 B2 | 7/2004 | Strickland, Jr. |
| 6,761,167 B1 | 7/2004 | Nadjafizadeh et al. |
| 6,761,168 B1 | 7/2004 | Nadjafizadeh et al. |
| 6,789,541 B2 | 9/2004 | Olsen et al. |
| 6,796,305 B1 | 9/2004 | Banner et al. |
| 6,810,876 B2 | 11/2004 | Berthon-Jones |
| 6,814,074 B1 | 11/2004 | Nadjafizadeh et al. |
| 6,820,613 B2 | 11/2004 | Wenkebach et al. |
| 6,820,618 B2 | 11/2004 | Banner et al. |
| 6,823,866 B2 | 11/2004 | Jafari et al. |
| 6,837,242 B2 | 1/2005 | Younes |
| 6,843,250 B2 | 1/2005 | Efrati |
| 6,866,040 B1 | 3/2005 | Bourdon |
| 6,868,346 B2 | 3/2005 | Larson et al. |
| 6,874,503 B2 | 4/2005 | Rydgren |
| 6,910,480 B1 | 6/2005 | Berthon-Jones |
| 6,910,481 B2 | 6/2005 | Kimmel et al. |
| 6,920,875 B1 | 7/2005 | Hill et al. |
| 6,920,877 B2 | 7/2005 | Remmers et al. |
| 6,932,084 B2 | 8/2005 | Estes et al. |
| 6,945,248 B2 | 9/2005 | Berthon-Jones |
| 6,948,497 B2 | 9/2005 | Zdrojkowski et al. |
| 6,960,854 B2 | 11/2005 | Nadjafizadeh et al. |
| 6,962,155 B1 | 11/2005 | Sinderby |
| 6,986,347 B2 | 1/2006 | Hickle |
| 7,000,612 B2 * | 2/2006 | Jafari et al. ............... 128/204.21 |
| 7,008,380 B1 | 3/2006 | Rees et al. |
| 7,013,892 B2 | 3/2006 | Estes et al. |
| 7,017,576 B2 | 3/2006 | Olsen et al. |
| 7,036,504 B2 | 5/2006 | Wallace et al. |
| 7,040,320 B2 | 5/2006 | Fjeld et al. |
| 7,055,522 B2 | 6/2006 | Berthon-Jones |
| 7,066,173 B2 | 6/2006 | Banner et al. |
| 7,073,501 B2 | 7/2006 | Remmers et al. |
| 7,077,131 B2 | 7/2006 | Hansen |
| 7,081,095 B2 | 7/2006 | Lynn et al. |
| RE39,225 E | 8/2006 | Isaza et al. |
| 7,089,936 B2 | 8/2006 | Madaus et al. |
| 7,092,757 B2 | 8/2006 | Larson et al. |
| 7,100,607 B2 | 9/2006 | Zdrojkowski et al. |
| 7,100,608 B2 | 9/2006 | Brewer et al. |
| 7,100,609 B2 | 9/2006 | Berthon-Jones et al. |
| 7,107,991 B2 | 9/2006 | Kolobow |
| 7,117,438 B2 | 10/2006 | Wallace et al. |
| 7,137,389 B2 | 11/2006 | Berthon-Jones |
| 7,152,598 B2 | 12/2006 | Morris et al. |
| 7,168,429 B2 | 1/2007 | Matthews et al. |
| 7,195,028 B2 | 3/2007 | Basset et al. |
| 7,210,478 B2 | 5/2007 | Banner et al. |
| 7,229,430 B2 | 6/2007 | Hickle et al. |
| 7,267,122 B2 | 9/2007 | Hill |
| 7,270,126 B2 | 9/2007 | Wallace et al. |
| 7,275,540 B2 | 10/2007 | Bolam et al. |
| 7,296,573 B2 | 11/2007 | Estes et al. |
| 7,297,119 B2 | 11/2007 | Westbrook et al. |
| 7,331,343 B2 | 2/2008 | Schmidt et al. |
| 7,353,824 B1 | 4/2008 | Forsyth et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| 7,398,115 B2 | 7/2008 | Lynn |
| 7,406,870 B2 | 8/2008 | Seto |
| 7,428,902 B2 | 9/2008 | Du et al. |
| 7,448,381 B2 | 11/2008 | Sasaki et al. |
| 7,455,583 B2 | 11/2008 | Taya et al. |
| 7,460,959 B2 | 12/2008 | Jafari |
| 7,475,685 B2 | 1/2009 | Dietz et al. |
| 7,487,773 B2 | 2/2009 | Li |
| 7,509,957 B2 | 3/2009 | Duquette et al. |
| 7,527,056 B2 | 5/2009 | Turiello |
| 7,533,671 B2 | 5/2009 | Gonzalez et al. |
| 7,621,269 B2 | 11/2009 | Turiello |
| 7,644,713 B2 | 1/2010 | Berthon-Jones |
| 7,654,802 B2 | 2/2010 | Crawford, Jr. et al. |
| 7,661,428 B2 | 2/2010 | Berthon-Jones |
| 7,673,629 B2 | 3/2010 | Turiello |
| 7,677,247 B2 | 3/2010 | Turiello |
| 7,694,677 B2 | 4/2010 | Tang |
| 7,694,678 B2 | 4/2010 | Turiello |
| 7,717,112 B2 | 5/2010 | Sun et al. |
| 7,717,113 B2 | 5/2010 | Andrieux |
| D618,356 S | 6/2010 | Ross |
| 7,770,578 B2 | 8/2010 | Estes et al. |
| 7,784,461 B2 | 8/2010 | Figueiredo et al. |
| 7,810,496 B2 | 10/2010 | Estes et al. |
| 7,810,497 B2 | 10/2010 | Pittman et al. |
| 7,814,906 B2 | 10/2010 | Moretti |
| 7,823,588 B2 | 11/2010 | Hansen |
| 7,827,988 B2 | 11/2010 | Matthews et al. |
| 7,855,716 B2 | 12/2010 | McCreary et al. |
| 7,856,979 B2 | 12/2010 | Doshi et al. |
| D632,796 S | 2/2011 | Ross et al. |
| D632,797 S | 2/2011 | Ross et al. |
| 7,882,835 B2 | 2/2011 | Eger et al. |
| 7,886,739 B2 | 2/2011 | Soliman et al. |
| 7,886,740 B2 | 2/2011 | Thomas et al. |
| 7,891,354 B2 | 2/2011 | Farbarik |
| 7,893,560 B2 | 2/2011 | Carter |
| 7,905,231 B2 | 3/2011 | Chalvignac |
| 7,918,222 B2 | 4/2011 | Chen |
| 7,918,223 B2 | 4/2011 | Soliman et al. |
| 7,920,067 B2 | 4/2011 | Durtschi et al. |
| 7,928,852 B2 | 4/2011 | Durtschi et al. |
| D638,852 S | 5/2011 | Skidmore et al. |
| 7,934,499 B2 | 5/2011 | Berthon-Jones |
| 7,938,114 B2 | 5/2011 | Matthews et al. |
| 7,963,283 B2 | 6/2011 | Sinderby |
| 7,984,712 B2 | 7/2011 | Soliman et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| 8,002,154 B2 | 8/2011 | Fontela et al. |
| D645,158 S | 9/2011 | Sanchez et al. |
| 8,021,309 B2 | 9/2011 | Zilberg |
| 8,021,310 B2 | 9/2011 | Sanborn et al. |
| 8,033,280 B2 | 10/2011 | Heinonen |
| D649,157 S | 11/2011 | Skidmore et al. |

| | | |
|---|---|---|
| 8,051,853 B2 | 11/2011 | Berthon-Jones |
| 8,070,709 B2 | 12/2011 | Childers |
| 8,083,677 B2 | 12/2011 | Rohde |
| D652,521 S | 1/2012 | Ross et al. |
| D652,936 S | 1/2012 | Ross et al. |
| 8,105,310 B2 | 1/2012 | Klein |
| D653,749 S | 2/2012 | Winter et al. |
| 8,113,062 B2 | 2/2012 | Graboi et al. |
| 8,122,885 B2 | 2/2012 | Berthon-Jones et al. |
| D655,405 S | 3/2012 | Winter et al. |
| D655,809 S | 3/2012 | Winter et al. |
| D656,237 S | 3/2012 | Sanchez et al. |
| 8,136,521 B2 | 3/2012 | Matthews et al. |
| 8,152,116 B2 | 4/2012 | Westberg |
| RE43,398 E | 5/2012 | Honkonen et al. |
| 8,181,643 B2 | 5/2012 | Friedberg |
| 8,181,648 B2 | 5/2012 | Perine et al. |
| 8,181,649 B2 | 5/2012 | Brunner |
| 8,187,184 B2 | 5/2012 | Muller et al. |
| 8,210,173 B2 | 7/2012 | Vandine |
| 8,210,174 B2 | 7/2012 | Farbarik |
| 8,211,128 B1 | 7/2012 | Facundus et al. |
| 8,216,159 B1 | 7/2012 | Leiboff |
| 8,217,218 B2 | 7/2012 | Court et al. |
| 8,225,796 B2 | 7/2012 | Davenport et al. |
| 8,235,930 B1 | 8/2012 | McCall |
| 8,240,684 B2 | 8/2012 | Ross et al. |
| 8,251,923 B2 | 8/2012 | Carrez et al. |
| 8,256,418 B2 | 9/2012 | Bassin |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,288,607 B2 | 10/2012 | Court et al. |
| 8,302,600 B2 | 11/2012 | Andrieux et al. |
| 8,302,602 B2 | 11/2012 | Andrieux et al. |
| 2002/0014240 A1 | 2/2002 | Truschel |
| 2002/0053345 A1 | 5/2002 | Jafari et al. |
| 2002/0185126 A1 | 12/2002 | Krebs |
| 2003/0010339 A1 | 1/2003 | Banner et al. |
| 2003/0158466 A1 | 8/2003 | Lynn et al. |
| 2003/0159695 A1 | 8/2003 | Younes |
| 2003/0221689 A1 | 12/2003 | Berthon-Jones |
| 2004/0050387 A1 | 3/2004 | Younes |
| 2004/0074492 A1 | 4/2004 | Berthon-Jones |
| 2004/0089561 A1 | 5/2004 | Herman |
| 2004/0163648 A1 | 8/2004 | Burton |
| 2004/0187870 A1 | 9/2004 | Matthews et al. |
| 2005/0039748 A1 | 2/2005 | Andrieux |
| 2005/0109340 A1 | 5/2005 | Tehrani |
| 2005/0139212 A1 | 6/2005 | Bourdon |
| 2005/0172965 A1 | 8/2005 | Thulin |
| 2005/0188991 A1 | 9/2005 | Sun et al. |
| 2005/0241639 A1 | 11/2005 | Zilberg |
| 2006/0000475 A1 | 1/2006 | Matthews et al. |
| 2006/0011200 A1 | 1/2006 | Remmers et al. |
| 2006/0086357 A1 | 4/2006 | Soliman et al. |
| 2006/0102180 A1 | 5/2006 | Berthon-Jones |
| 2006/0112959 A1 | 6/2006 | Mechlenburg et al. |
| 2006/0118112 A1 | 6/2006 | Cattano et al. |
| 2006/0144144 A1 | 7/2006 | Seto |
| 2006/0150974 A1 | 7/2006 | Berthon-Jones |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0174883 A1 | 8/2006 | Aylsworth et al. |
| 2006/0189880 A1 | 8/2006 | Lynn et al. |
| 2006/0195041 A1 | 8/2006 | Lynn et al. |
| 2006/0201505 A1 | 9/2006 | Remmers et al. |
| 2006/0217633 A1 | 9/2006 | Glocker et al. |
| 2006/0235324 A1 | 10/2006 | Lynn |
| 2006/0241708 A1 | 10/2006 | Boute |
| 2006/0247508 A1 | 11/2006 | Fennell |
| 2006/0249150 A1 | 11/2006 | Dietz et al. |
| 2006/0249156 A1 | 11/2006 | Moretti |
| 2006/0254588 A1 | 11/2006 | Brewer et al. |
| 2006/0264762 A1 | 11/2006 | Starr |
| 2006/0272642 A1 | 12/2006 | Chalvignac |
| 2006/0278218 A1 | 12/2006 | Hoffman |
| 2007/0000494 A1 | 1/2007 | Banner et al. |
| 2007/0017515 A1 | 1/2007 | Wallace et al. |
| 2007/0027375 A1 | 2/2007 | Melker et al. |
| 2007/0028921 A1 | 2/2007 | Banner et al. |
| 2007/0044796 A1* | 3/2007 | Zdrojkowski et al. ... 128/204.18 |
| 2007/0068530 A1 | 3/2007 | Pacey |
| 2007/0072541 A1 | 3/2007 | Daniels, II et al. |
| 2007/0077200 A1 | 4/2007 | Baker |
| 2007/0089738 A1 | 4/2007 | Soliman et al. |
| 2007/0093721 A1 | 4/2007 | Lynn et al. |
| 2007/0101992 A1 | 5/2007 | Soliman et al. |
| 2007/0129647 A1 | 6/2007 | Lynn |
| 2007/0135736 A1 | 6/2007 | Addington et al. |
| 2007/0144522 A1 | 6/2007 | Eger et al. |
| 2007/0149860 A1 | 6/2007 | Lynn et al. |
| 2007/0157931 A1 | 7/2007 | Parker et al. |
| 2007/0163579 A1 | 7/2007 | Li et al. |
| 2007/0191688 A1 | 8/2007 | Lynn |
| 2007/0191697 A1 | 8/2007 | Lynn et al. |
| 2007/0215154 A1 | 9/2007 | Borrello |
| 2007/0221224 A1 | 9/2007 | Pittman et al. |
| 2007/0227537 A1 | 10/2007 | Bemister et al. |
| 2007/0251532 A1 | 11/2007 | Friedberg |
| 2007/0272241 A1 | 11/2007 | Sanborn et al. |
| 2007/0277823 A1 | 12/2007 | Al-Ali et al. |
| 2007/0283958 A1 | 12/2007 | Naghavi |
| 2007/0284361 A1 | 12/2007 | Nadjafizadeh et al. |
| 2008/0000478 A1 | 1/2008 | Matthiessen et al. |
| 2008/0000479 A1 | 1/2008 | Elaz et al. |
| 2008/0041382 A1 | 2/2008 | Matthews et al. |
| 2008/0041383 A1 | 2/2008 | Matthews et al. |
| 2008/0051674 A1 | 2/2008 | Davenport et al. |
| 2008/0053441 A1 | 3/2008 | Gottlib et al. |
| 2008/0053442 A1 | 3/2008 | Estes et al. |
| 2008/0053443 A1 | 3/2008 | Estes et al. |
| 2008/0053444 A1 | 3/2008 | Estes et al. |
| 2008/0066752 A1 | 3/2008 | Baker et al. |
| 2008/0066753 A1 | 3/2008 | Martin et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0081974 A1 | 4/2008 | Pav |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0168988 A1 | 7/2008 | Lu |
| 2008/0178880 A1 | 7/2008 | Christopher et al. |
| 2008/0178882 A1 | 7/2008 | Christopher et al. |
| 2008/0185002 A1 | 8/2008 | Berthon-Jones et al. |
| 2008/0200775 A1 | 8/2008 | Lynn |
| 2008/0200819 A1 | 8/2008 | Lynn et al. |
| 2008/0221469 A1 | 9/2008 | Shevchuk |
| 2008/0251079 A1 | 10/2008 | Richey |
| 2008/0295837 A1 | 12/2008 | McCormick et al. |
| 2008/0302359 A1 | 12/2008 | Loomas et al. |
| 2009/0014007 A1 | 1/2009 | Brambilla et al. |
| 2009/0050153 A1* | 2/2009 | Brunner ............... 128/204.23 |
| 2009/0082653 A1 | 3/2009 | Rohde |
| 2009/0088613 A1 | 4/2009 | Marttila et al. |
| 2009/0093697 A1 | 4/2009 | Mir et al. |
| 2009/0137927 A1 | 5/2009 | Miller |
| 2009/0149730 A1 | 6/2009 | McCrary |
| 2009/0165795 A1 | 7/2009 | Nadjafizadeh et al. |
| 2009/0171176 A1 | 7/2009 | Andersohn |
| 2009/0171226 A1 | 7/2009 | Campbell et al. |
| 2009/0178675 A1 | 7/2009 | Turiello |
| 2009/0178676 A1 | 7/2009 | Villax et al. |
| 2009/0194100 A1 | 8/2009 | Minagi |
| 2009/0205661 A1 | 8/2009 | Stephenson et al. |
| 2009/0205663 A1 | 8/2009 | Vandine et al. |
| 2009/0229605 A1 | 9/2009 | Efrati et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |

| Publication No. | Date | Inventor |
|---|---|---|
| 2009/0250061 A1 | 10/2009 | Marasigan |
| 2009/0272382 A1 | 11/2009 | Euliano et al. |
| 2009/0281481 A1 | 11/2009 | Harding |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0308398 A1 | 12/2009 | Ferdinand et al. |
| 2009/0314294 A1 | 12/2009 | Chalvignac |
| 2009/0318851 A1 | 12/2009 | Schenck |
| 2010/0011307 A1 | 1/2010 | Desfossez et al. |
| 2010/0018529 A1 | 1/2010 | Chalvignac |
| 2010/0024819 A1* | 2/2010 | Tiedje ............... 128/204.23 |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0065057 A1* | 3/2010 | Berthon-Jones ......... 128/204.23 |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078018 A1 | 4/2010 | Heinonen |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0081958 A1 | 4/2010 | She |
| 2010/0101574 A1 | 4/2010 | Bassin |
| 2010/0101576 A1 | 4/2010 | Berthon-Jones |
| 2010/0116276 A1 | 5/2010 | Bayasi |
| 2010/0137737 A1 | 6/2010 | Addington et al. |
| 2010/0139660 A1 | 6/2010 | Adahan |
| 2010/0147303 A1 | 6/2010 | Jafari et al. |
| 2010/0186741 A1 | 7/2010 | Aylsworth et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0234758 A1 | 9/2010 | de Menezes |
| 2010/0236553 A1 | 9/2010 | Jafari et al. |
| 2010/0236555 A1 | 9/2010 | Jafari et al. |
| 2010/0242961 A1 | 9/2010 | Mougel et al. |
| 2010/0252048 A1 | 10/2010 | Young et al. |
| 2010/0258123 A1 | 10/2010 | Somaiya et al. |
| 2010/0262038 A1 | 10/2010 | Tan et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2010/0331768 A1 | 12/2010 | Hedmann et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0034863 A1 | 2/2011 | Hoffa |
| 2011/0041849 A1 | 2/2011 | Chen et al. |
| 2011/0041850 A1 | 2/2011 | Vandine et al. |
| 2011/0061648 A1 | 3/2011 | Durtschi et al. |
| 2011/0071367 A1 | 3/2011 | Court et al. |
| 2011/0077549 A1 | 3/2011 | Kitai et al. |
| 2011/0100373 A1 | 5/2011 | Efrati et al. |
| 2011/0125052 A1 | 5/2011 | Davenport et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132363 A1 | 6/2011 | Chalvignac |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0178427 A1 | 7/2011 | Tan et al. |
| 2011/0196251 A1 | 8/2011 | Jourdain et al. |
| 2011/0201956 A1 | 8/2011 | Alferness et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0220112 A1 | 9/2011 | Connor |
| 2011/0226250 A1 | 9/2011 | LaBollita et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2011/0284003 A1 | 11/2011 | Douglas et al. |
| 2011/0290246 A1 | 12/2011 | Zachar |
| 2011/0293706 A1 | 12/2011 | Ludwig et al. |
| 2011/0313689 A1 | 12/2011 | Holley et al. |
| 2012/0000466 A1 | 1/2012 | Rapoport |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0006328 A1 | 1/2012 | Berthon-Jones |
| 2012/0022441 A1 | 1/2012 | Kelly et al. |
| 2012/0029317 A1 | 2/2012 | Doyle et al. |
| 2012/0030611 A1 | 2/2012 | Skidmore |
| 2012/0060835 A1 | 3/2012 | Mashak |
| 2012/0060841 A1 | 3/2012 | Crawford, Jr. et al. |
| 2012/0065533 A1 | 3/2012 | Carrillo, Jr. et al. |
| 2012/0071729 A1 | 3/2012 | Doyle et al. |
| 2012/0083729 A1 | 4/2012 | Childers |
| 2012/0090610 A1 | 4/2012 | O'Connor et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0139734 A1 | 6/2012 | Olde et al. |
| 2012/0150057 A1 | 6/2012 | Mantri |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0215081 A1 | 8/2012 | Euliano et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |

FOREIGN PATENT DOCUMENTS

| | | |
|---|---|---|
| EP | 1270036 | 1/2003 |
| WO | WO 94/23780 A | 10/1994 |
| WO | WO 98/06449 A | 2/1998 |
| WO | WO 00/10634 A | 3/2000 |
| WO | WO 00/45880 A | 8/2000 |
| WO | WO 01/74430 A | 10/2001 |
| WO | WO 02/28460 A | 4/2002 |
| WO | WO 03/055552 A1 | 7/2003 |
| WO | WO 04000114 | 12/2003 |

| | | |
|---|---|---|
| WO | WO 2004/084980 A | 10/2004 |
| WO | WO 2005/105189 | 11/2005 |
| WO | WO 2006/137784 | 12/2006 |
| WO | WO 2007145948 | 12/2007 |
| WO | WO 2009123981 | 10/2009 |

OTHER PUBLICATIONS

PCT International Search Report and Written Opinion in Application PCT/2009/038815, mailed Jul. 1, 2009, 14 pgs.
PCT International Search Report and Written Opinion in Application PCT/US09/038811, mailed Jun. 7, 2009, 13 pgs.
PCT International Search Report and Written Opinion in Application PCT/US2009/038819, mailed Jun. 26, 2009, 12 pgs.
PCT International Search Report and Written Opinion in Application PCT/US2009/038820, mailed Jul. 22, 2009, 14 pgs.
PCT International Search Report and Written Opinion in Application PCT/US2009038818, mailed Jul. 14, 2009, 15 pgs.
PCT International Search Report and Written Opinion in Application PCT/US201/0026618, mailed Jun. 22, 2010, 19 pgs.
PCT International Search Report and Written Opinion in Application PCT/US2010/025485, mailed Feb. 27, 2009, 8 pgs.
U.S. Appl. No. 12/242,741, Notice of Allowance mailed Jun. 5, 2012, 5 pgs.
U.S. Appl. No. 12/242,741, Office Action mailed Jan. 10, 2012, 7 pgs.
U.S. Appl. No. 12/242,756, Notice of Allowance mailed Jun. 5, 2012, 5 pgs.
U.S. Appl. No. 12/242,756, Office Action mailed Jan. 10, 2012, 7 pgs.
U.S. Appl. No. 12/334,354, Notice of Allowance mailed Jan. 27, 2012, 7 pgs.
U.S. Appl. No. 12/408,408, Notice of Allowance mailed Jun. 4, 2012, 10 pgs.
U.S. Appl. No. 12/408,414, Office Action mailed Jun. 20, 2012, 9 pgs.
U.S. Appl. No. 12/414,419, Office Action mailed Jan. 20, 2012, 15 pgs.
U.S. Appl. No. 12/414,419, Office Action mailed Jul. 18, 2012, 16 pgs.
U.S. Appl. No. 12/242,756, Supplemental Notice of Allowability mailed Aug. 27, 2012, 2 pgs.
U.S. Appl. No. 12/242,741, Supplemental Notice of Allowability mailed Aug. 27, 2012, 2 pgs.
U.S. Appl. No. 12/408,414, Amendment and Response filed Sep. 5, 2012, 7 pgs.
U.S. Appl. No. 12/414,419, Amendment and Response filed Aug. 27, 2012, 8 pgs.
Jafari, M. et al., "Robust Feedback Design for Proportional Assist Ventilation-System Dynamics and Problem Definition" Decision and Control, 2005 and 2005 European Control Conference. CDC-E CC '05. 44th IEEE Conference on Seville, Spain Dec. 12-15, 2005, pp. 4839-4844, XP010884460 DISBN: 978-0-7803-9567-1, the whole document.
U.S. Appl. No. 12/238,248, Office Action mailed Oct. 15, 2012, 12 pgs.
U.S. Appl. No. 12/238,248, Office Action mailed May 14, 2012, 12 pgs.
U.S. Appl. No. 12/334,354, Notice of Allowance mailed Oct. 5, 2012, 5 pgs.
U.S. Appl. No. 12/395,332, Office Action mailed Sep. 13, 2012, 9 pgs.
U.S. Appl. No. 12/414,419, Notice of Allowance mailed Sep. 19, 2012, 8 pgs.
U.S. Appl. No. 12/395,332, Notice of Allowance mailed Dec. 24, 2012, 8 pgs.
U.S. Appl. No. 12/408,414, Notice of Allowance mailed Dec. 10, 2012, 10 pgs.
U.S. Appl. No. 12/414,419, Notice of Allowance mailed Jan. 8, 2013, 7 pgs.
U.S. Appl. No. 12/238,248, Advisory Action mailed Jan. 4, 2013, 3 pgs.

* cited by examiner

LEAK-COMPENSATED PROPORTIONAL ASSIST VENTILATION

RELATED APPLICATIONS

This application is a divisional application of U.S. patent application Ser. No. 12/408,408 (now U.S. Pat. No. 8,267, 085), entitled "LEAK-COMPENSATED PROPORTIONAL ASSIST VENTILATION," filed on Mar. 20, 2009, the complete disclosure of which is hereby incorporated by reference in its entirety.

INTRODUCTION

In mechanical ventilation, proportional assist (PA) refers to a type of ventilation in which the ventilator acts as an inspiratory amplifier that provides pressure support based on the patient's effort. The degree of amplification (the "support setting") is set by an operator, for example as a percentage based on the patient's effort. In one implementation of PA ventilation, the ventilator may continuously monitor the patient's instantaneous inspiratory flow and instantaneous net lung volume, which are indicators of the patient's inspiratory effort. These signals, together with ongoing estimates of the patient's lung compliance and lung resistance, allow the ventilator to compute the instantaneous pressure at a point in the ventilation circuit that assists the patient's inspiratory muscles to the degree selected by the operator as the support setting.

PA ventilation relies on certain physiological principles. The act of inspiration requires the patient's inspiratory muscles to develop a pressure gradient between the mouth and the alveoli sufficient to draw in breathing gas and inflate the lungs. Some of this pressure gradient is dissipated as gas travels through the artificial airway and the patient's conducting airways, and some of the pressure gradient is dissipated in the inflation of the lungs and thorax. Each element of pressure dissipation is characterized by a measurable property: the resistance of the artificial and patient airways, and the compliance (or elastance) of the lung and thorax.

The ventilator providing PA ventilation uses specific information, including resistance of the artificial airway, resistance of the patient's airways, lung compliance, instantaneous inspiratory flow and net lung volume, and the support setting to compute the instantaneous pressure to be applied at the wye. The ventilator may estimate patient lung resistance and lung compliance, for example approximately every four to ten breaths. In one implementation, every computational cycle (e.g., 5 milliseconds), the ventilator estimates lung flow, based on an estimate of circuit flow, and lung volume, based on the integral value of estimated circuit flow.

PA ventilation begins inspiratory assist when flow (generated by the patient's inspiratory muscles) is detected. If the patient ceases inspiration, the assist also ceases. Once inspiratory flow begins, the ventilator monitors instantaneous flow and volume and applies the pressure calculated to deliver a proportion (determined by the support setting) of the total demand as determined by the patient's inspiratory effort. In Tube Compensation (TC) ventilation, the ventilator monitors instantaneous flow and volume and applies the pressure calculated to overcome a proportion (determined by the support setting) of the pressure losses dissipated across the resistance of the artificial airways (e.g., endotracheal tube).

The lung compliance and lung resistance of a patient may be collectively referred to as the respiratory mechanics of the lung or, simply, the patient's respiratory mechanics. Because PA relies on the patient's respiratory mechanics, more accurate determination of respiratory mechanics is essential to performance of the ventilator when providing PA.

Leak-Compensated Proportional Assist Ventilation

This disclosure describes systems and methods for compensating for leakage when during delivery of gas to a patient from a medical ventilator in a proportional assist (PA) mode. The technology described herein includes systems and methods that compensate the delivery of PA ventilation for leakage in the patient circuit by using leak-compensated lung flows as well as respiratory mechanics (lung compliance and lung resistance) estimated in a manner that compensates for elastic and inelastic leaks from the ventilation system.

In part, this disclosure describes a method of compensating for leakage in a ventilation system during delivery of gas from a medical ventilator providing PA to a patient. The method includes monitoring an instantaneous flow in the ventilation system based on one or more measurements of pressure and flow in ventilation system. Leakage from the system is modeled as a first leakage component through a first orifice of a fixed size and a second leakage component through a second orifice of a varying size, in which the first and second leakage components are different functions of instantaneous pressure in the ventilation system. A leak-compensated instantaneous lung flow of gas inhaled or exhaled by the patient is estimated based on the one or more measurements, the first leakage component and second leakage component. The leak-compensated lung flow and a predetermined respiratory mechanics model are used to estimate a leak-compensated lung compliance and a leak-compensated lung resistance. A pressure to be delivered to the patient is then calculated based on the leak-compensated lung flow, the leak-compensated lung compliance and the leak-compensated lung resistance.

This disclosure describes a method of compensating for leakage in a ventilation tubing system during delivery of gas from a medical ventilator to a patient. The method includes receiving a support setting identifying an amount of proportional assistance to provide to the patient. An inelastic leakage in the ventilation system is identified as a first function of at least one of a pressure measurement and a flow measurement in the ventilation system. An elastic leakage in the ventilation system is also identified as a second function of at least one of the pressure measurement and the flow measurement in the ventilation system. The circuit compliance and circuit resistance of the ventilation tubing system is then used along with estimated lung compliance of the patient and estimated lung resistance of the patient based on the inelastic leakage, the elastic leakage, the circuit compliance, circuit resistance and the at least one of the pressure measurement and the flow measurement in the ventilation system. Ventilation is then delivered to the patient based on estimated patient effort and the support setting, in which the patient effort is determined from estimated lung flow using the inelastic leakage, the elastic leakage, the lung compliance and the lung resistance.

The disclosure also describes a pressure support system that includes a pressure generating system adapted to generate a flow of breathing gas and a ventilation tubing system including a patient interface device for connecting the pressure generating system to a patient. One or more sensors are operatively coupled to the pressure generating system or the ventilation system, in which each sensor capable of generating an output indicative of a pressure of the breathing gas. A leak estimation module is provided that identifies leakage in the ventilation system and compensates the calculation of lung flow for the estimated leakage in the system. A respiratory mechanics calculation module is further provided that generates a leak-compensated lung compliance and a leak-compensated lung resistance based on the leakage and at least one output indicative of a pressure of the breathing gas. The system further includes a proportional assistance ventilation module that causes the pressure generating system to provide ventilation to the patient based on patient effort and a support setting, in which the patient effort is determined from estimated lung flow using the leakage, the leak-compensated lung compliance and the leak-compensated lung resistance.

The disclosure flutter describes a PA ventilation controller for a medical ventilator. The controller includes a microprocessor, a module that compensates calculations of lung compliance and lung resistance based on instantaneous elastic leakage and instantaneous inelastic leakage of breathing gas from a ventilation system, and a pressure control module that provides proportional assist ventilation based on the compensated lung compliance and lung resistance.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of described technology and are not meant to limit the scope of the invention as claimed in any manner, which scope shall be based on the claims appended hereto.

DETAILED DESCRIPTION

Although the techniques introduced above and discussed in detail below may be implemented for a variety of medical devices, the present disclosure will discuss the implementation of these techniques in the context of a medical ventilator providing pressure assist (PA) ventilation to a human patient. The reader will understand that the technology described in the context of a medical ventilator for human patients could be adapted for use with other systems such as ventilators for non-human patients and general gas transport systems in which leaks may cause a degradation of performance.

Figure 1:
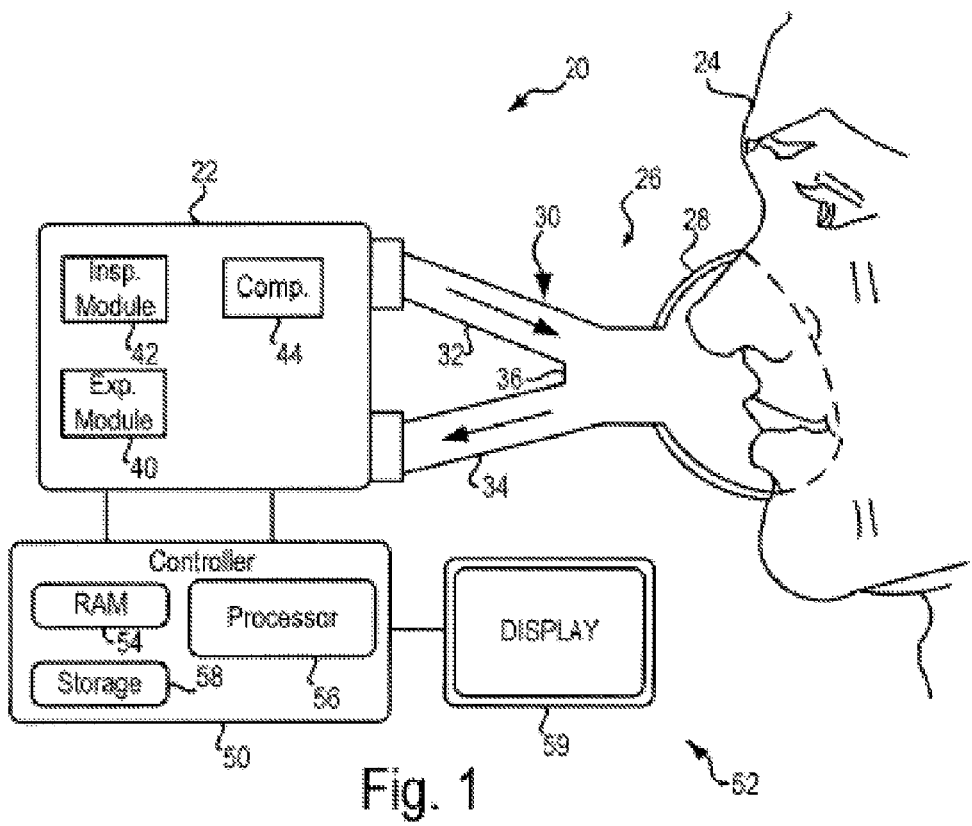
FIG. 1 illustrates an embodiment of a ventilator connected to a human patient.

FIG. 1 illustrates an embodiment of a ventilator 20 connected to a human patient 24. Ventilator 20 includes a pneumatic system 22 (also referred to as a pressure generating system 22) for circulating breathing gases to and from patient 24 via the ventilation tubing system 26, which couples the patient to the pneumatic system via physical patient interface 28 and ventilator circuit 30. Ventilator circuit 30 could be a dual-limb or single-limb circuit for carrying gas to and from the patient. In a dual-limb embodiment as shown, a wye fitting 36 may be provided as shown to couple the patient interface 28 to the inspiratory limb 32 and the expiratory limb 34 of the circuit 30.

The present systems and methods have proved particularly advantageous in noninvasive settings, such as with facial breathing masks, as those settings typically are more susceptible to leaks. However, leaks do occur in a variety of settings, and the present description contemplates that the patient interface may be invasive or non-invasive, and of any configuration suitable for communicating a flow of breathing gas from the patient circuit to an airway of the patient. Examples of suitable patient interface devices include a nasal mask, nasal/oral mask (which is shown in FIG. 1), nasal prong, full-face mask, tracheal tube, endotracheal tube, nasal pillow, etc.

Pneumatic system 22 may be configured in a variety of ways. In the present example, system 22 includes an expiratory module 40 coupled with an expiratory limb 34 and an inspiratory module 42 coupled with an inspiratory limb 32. Compressor 44 or another source(s) of pressurized gas (e.g., air and oxygen) is coupled with inspiratory module 42 to provide a gas source for ventilatory support via inspiratory limb 32.

The pneumatic system may include a variety of other components, including sources for pressurized air and/or oxygen, mixing modules, valves, sensors, tubing, accumulators, filters, etc. Controller 50 is operatively coupled with pneumatic system 22, signal measurement and acquisition systems, and an operator interface 52 may be provided to enable an operator to interact with the ventilator (e.g., change ventilator settings, select operational modes, view monitored parameters, etc.). Controller 50 may include memory 54, one or more processors 56, storage 58, and/or other components of the type commonly found in command and control computing devices.

The memory 54 is computer-readable storage media that stores software that is executed by the processor 56 and which controls the operation of the ventilator 20. In an embodiment, the memory 54 comprises one or more solid-state storage devices such as flash memory chips. In an alternative embodiment, the memory 54 may be mass storage connected to the processor 56 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 56. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As described in more detail below, controller 50 issues commands to pneumatic system 22 in order to control the breathing assistance provided to the patient by the ventilator. The specific commands may be based on inputs received from an operator, the patient 24, the pneumatic system 22 and sensors, the operator interface 52 and/or other components of the ventilator. In the depicted example, operator interface includes a display 59 that is touch-sensitive, enabling the display to serve both as an input and output device.

Figure 2:
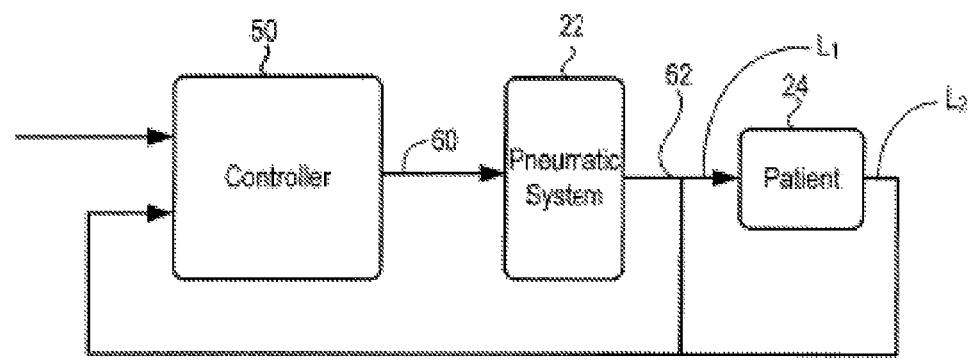
FIG. 2 schematically depicts example systems and methods of ventilator control.

FIG. 2 schematically depicts exemplary systems and methods of ventilator control. As shown, controller 50 issues control commands 60 to drive pneumatic system 22 and thereby circulate breathing gas to and from patient 24. The depicted schematic interaction between pneumatic system 22 and patient 24 may be viewed in terms of pressure and/or flow "signals." For example, signal 62 may be an increased pressure which is applied to the patient via inspiratory limb 32. Control commands 60 are based upon inputs received at controller 50 which may include, among other things, inputs from operator interface 52, and feedback from pneumatic system 22 (e.g., from pressure/flow sensors) and/or sensed from patient 24.

In an embodiment, before the respiratory mechanics of a patient can be determined, the mechanics of the ventilation tubing system may be determined. For example, when modeling the delivery of gas to and from a patient 24 via a closed-circuit ventilator, one simple assumption is that compliance of the ventilator circuit 30 (the "circuit compliance") is fixed and that all gas injected into the ventilator circuit 30 that does not exit the circuit 30 via the expiratory limb 34 (in a dual-limb embodiment) fills the circuit as well as the patient's lungs and causes an increase in pressure. As gas is injected ($L_1$), the lung responds to the increased gas pressure in the circuit 30 by expanding. The amount the lung expands is proportional to the lung compliance and is defined as a function of gas pressure differential (e.g., lung compliance=volume delivered/pressure difference). As discussed in greater detail below, this assumption is not valid when leaks are present.

The term circuit compliance is used to refer to the relationship between the amount the pressure in the ventilator circuit 30 (or ventilator circuit 30 and attached patient interface 28, depending on how the compliance is determined) and changes in volume delivered into the circuit. In an embodiment, the circuit compliance may be estimated by pressurizing the ventilator circuit 30 (or circuit 30 and interface 28 combination) when flow to the patient is blocked and measuring the volume of additional gas introduced to cause the pressure change (compliance=volume delivered/pressure difference).

The term circuit resistance is used to refer to the amount the pressure changes between two sites upstream and downstream the ventilator circuit as a function of volumetric flow rate through that circuit. Circuit resistance may be modeled as a two-parameter function of flow and several methods for modeling and calculating circuit resistance are known in the art. For example, in an embodiment, the circuit resistance may be estimated by passing several fixed flow rates through the circuit and measuring the pressure difference between certain upstream and downstream sites and finding the best curve fit to the collected data.

Methods of determining circuit compliance and circuit resistance (such as those described above) may be executed by the operator prior to attaching the patient to the ventilator as part of the set up of the ventilator 20 to provide therapy. Other methods of determining circuit compliance and/or resistance are also known and could be adapted for use with the disclosed leak-compensation systems and methods described herein.

In many cases, it may be desirable to establish a baseline pressure and/or flow trajectory for a given respiratory therapy session. The volume of breathing gas delivered to the patient's lung ($L_1$) and the volume of the gas exhaled by the patient ($L_2$) are measured or determined, and the measured or predicted/estimated leaks are accounted for to ensure accurate delivery and data reporting and monitoring. Accordingly, the more accurate the leak estimation, the better the baseline calculation of delivered and exhaled flow rates and volumes.

Errors may be introduced due to leaks in the ventilation tubing system 26. The term ventilation tubing system 26 is used herein to describe the ventilator circuit 30, any equipment attached to or used in the ventilator circuit 30 such as water traps, monitors, drug delivery devices, etc. (not shown), and the patient interface 28. Depending on the embodiment, this may include some equipment contained in the inspiration module 42 and/or the expiration module 40. When referring to leaks in or from the ventilation tubing system 26, such leaks include leaks within the tubing system 26 and leaks where the tubing system 26 connects to the pressure generator 22 or the patient 24. Thus, leaks from the ventilation tubing system 26 include leaks from the ventilator circuit 30, leaks from the patient interface 28 (e.g., masks are often provided with holes or other pressure relief devices through which some leakage may occur), leaks from the point of connection of the patient interface 28 to the patient 24 (e.g., leaks around the edges of a mask due to a poor fit or patient movement), and leaks from the point of connection of the patient interface 28 to the circuit 30 (e.g., due to a poor connection between the patient interface 28 and the circuit 30).

For the purpose of estimating how a leak flow rate changes based on changes in pressure in the ventilation tubing system 26, the instantaneous leak may be modeled as a leak through a single rigid orifice or opening of a fixed size in which that size is determined based on comparing the total flow into the inspiratory limb 32 and out of the expiratory limb 34. However, this leak model does not take into account any elastic component of leak source(s) in the system 26, that is how much of the area of any of the holes or openings in the ventilation tubing system 26 through which leakage occurs may change due to an increase or decrease in pressure.

It has been determined that not accounting for elastic leakage from the ventilation tubing system 26 can cause many problems. First, if only the inelastic/fixed orifice model is used to estimate leak, the subsequent errors caused by ignoring the elastic effects of any actual leaks end up generating inaccurate estimates of flow rates into the lung. This can cause the ventilator 20 to estimate gas volume delivered into the lung inaccurately when, in fact, the elastic leaks in the system 26 have let more gas escape than estimated. Second, if the elasticity of the leak source is ignored, any other calculation, estimate, or action that the ventilator 20 may perform which is affected by the leak estimate will be less accurate.

In the systems and methods described herein, the provision of PA ventilation is made more accurate by compensating for tubing system leakage. In the embodiments described herein fixed (rigid) and elastic components of the system leakage are used when determining the lung flow, net lung volume, lung compliance and lung resistance of the patient. This results in a more accurate determination of lung compliance and lung resistance and, therefore, ventilation of patients based on respiratory mechanics. While the systems and methods are presented in the context of specific leakage models, the technology described herein could be used to compensate the respiratory mechanics determined by any model for leakage using any type of mechanical ventilator or other device that provides gas.

Figure 3:
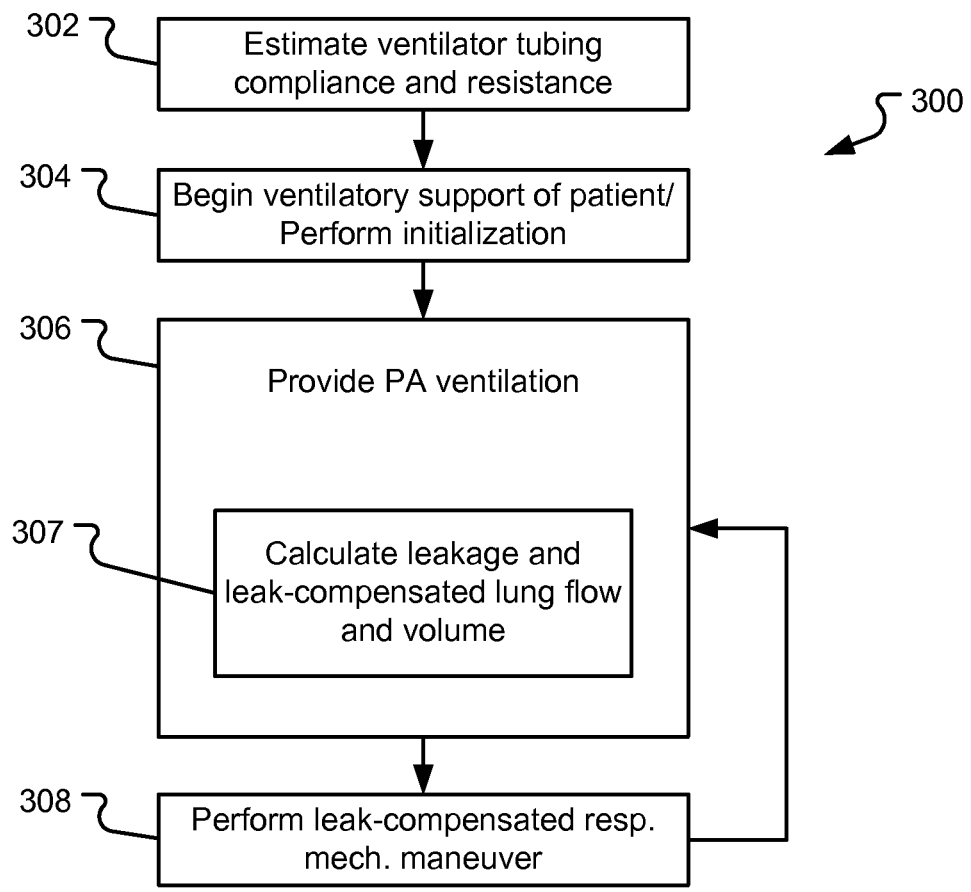
FIG. 3 illustrates an embodiment of a method of compensating for leakage in a ventilator providing pressure assistance to a patient.

FIG. 3 illustrates an embodiment of a method of compensating PA ventilation for leakage during delivery of gas from a medical ventilator to a patient. In the method 300 shown, a medical ventilator such as that described above with reference to FIGS. 1 and 2 is used to provide PA ventilation to a patient.

The method 300 illustrated starts with a circuit compliance and resistance operation 302. In that operation 302, the ventilator circuit compliance and resistance are estimated. In an embodiment, this may be performed prior to connecting the ventilator to the patient (as previously described). Alternatively, it may be dynamically determined periodically throughout the delivery of ventilatory support to the patient.

After the circuit compliance and resistance have been determined, the ventilator is connected to the patient and an initialization operation 304 is performed. In the initialization operation 304 the ventilator operates for an initialization or startup period in order to generate an initial estimate of lung compliance and lung resistance. If the ventilator already has some knowledge of the respiratory mechanics of the patient (e.g., the respiratory mechanics have been recently determined during provision of a different type of ventilation or an operator has provided initial settings for lung compliance and resistance), this operation 304 may be automatically or manually omitted in favor of the previously determined values.

A description of an embodiment of the initialization operation 304 is as follows. Because the ventilator does not know the patient's mechanics when the PA breath type is selected, it performs a startup routine to obtain initial data. In an embodiment, upon startup the ventilator delivers some number (e.g., two, four, etc.) of consecutive PA breaths, each of which includes an end-inspiratory maneuver that yields estimates of the patient's resistance and compliance. Using four training breaths for the initialization operation 304 as an example, the first breath is delivered using a predicted resistance for the artificial airway and conservative estimates for patient resistance and compliance. The predicted values may be determined based on known characteristics of the patient, such as based on the patient's ideal body weight (IBW), height, gender, age, physical condition, etc. Each of the following three PA breath's averages stepwise decreased physiologic values with the estimated resistance and compliance values from the previous breath, weighting earlier estimates less with each successive breath, and yielding more reliable estimates for lung resistance and lung compliance.

In an embodiment of the method 300, a leakage estimate may also be done prior to the initialization operation 304. Prior determination of leak parameters allows for estimates of respiratory mechanics to be made. This may include delivering pressure-regulated breaths with specific settings or performing specific "leak maneuvers", that is a specified set of controlled actions on the part of the ventilator that allow leakage parameters to be identified and quantified, such as interrupting the therapeutic delivery of respiratory gas and holding or changing the pressure and flow, so that data concerning the leakage of the system during the controlled actions may be obtained. For example, a leak maneuver may include periodically holding the pressure and flow in the circuit constant while determining (based on a comparison of the measured flow into the inspiratory limb and the measured flow out of the expiratory limb via the exhalation valve) the net leakage from the system. In an embodiment, such a leak maneuver may be performed during specific parts of the respiratory phase, e.g., at the end of the expiratory phase. In yet another embodiment, a sequence of pressure-based test breaths is delivered with specific settings to determine leak parameters prior to execution of test breaths for respiratory mechanics determinations.

After the initialization operation 304, the ventilator provides ongoing PA ventilation to the patient in a PA ventilation operation 306. PA ventilation begins inspiratory assist when an inspiratory trigger is detected such as leak-compensated lung flow (generated by the patient's inspiratory muscles) exceeds a set sensitivity threshold. If the patient ceases inspiration, the assist also ceases. Once inspiratory flow begins, the ventilator monitors instantaneous flow and volume and applies the pressure calculated to deliver a proportion (determined by the support setting) of the total demand as determined by the patient's inspiratory effort.

During PA ventilation, pressure assistance is provided to the patient based on the patient's effort and the operator-selected support setting. PA ventilation determines how much to assist the patient's efforts based on one or more equations of motion used to describe the mechanics of the lung. Such equations use respiratory mechanics of the patient, e.g., lung resistance and lung compliance, and the circuit when calculating how much flow and/or pressure to provide. One example of an equation of motion for use in determining the pressure to provide during PA ventilation is as follows:

$$P_{aw}(t)=E\int Qdt+QR-P_m(t)$$

where $P_{aw}$ is the pressure measured at the patient interface, $P_m$ is the pressure generated by the inspiratory muscles of the patient which is may be used as the index of the patient's effort, E is the lung elastance (which is the inverse of lung compliance, i.e., $E=1/C$), Q is the instantaneous leak-compensated lung flow and R is the lung resistance. By manipulating this equation slightly, an equation for the amount of desired pressure assistance at the patient interface to provide can be obtained:

$$P_{aw}(t)=kE\int Qdt+kQR$$

where k is the % support setting based on the patient effort, $P_m$. The equations above are one example of how PA ventilation may be provided based on patient effort. PA ventilation is known in the art and any suitable technique or set of equations for determining the assistance to provide may be used.

As described above, the patient's effort is determined based on the pressure and leak-compensated lung flow in the circuit. In order to compensate for leakage in the circuit, in the method 300 shown the PA ventilation operation 306 includes the ongoing calculation of leakage while providing ventilation, as illustrated by the leakage calculation/compensation operation 307. As discussed in greater detail below with reference to FIG. 4, the leakage is calculated and the leak-compensated values for lung flow, current lung volume and net delivered lung flow may be determined taking into account the calculated leakage.

The method 300 also includes periodically or randomly performing a respiratory mechanics maneuver in order to recalculate the lung compliance and lung resistance of the patient. In an embodiment, the respiratory mechanics maneuver operation 308 is performed randomly once every four to ten PA breaths.

The respiratory mechanics maneuver operation 308 compensates for leakage as determined by the leakage calculation/compensation operation 307 when calculating the respiratory mechanics for the patient. This may include stabilizing the pressure and flow in the patient circuit based on the calculated leakage at that pressure so that the flow into the patient circuit is approximately equal to the calculated amount of gas leaking from the patient circuit at that pressure; a period of stable pressure during which there is no flow into or out of the patient's lungs even though there is leakage flow in the ventilator tubing system. The respiratory mechanics maneuver operation 308 may further include using leak-compensated values of lung flow and lung volume when determining the respiratory mechanics.

The newly determined values of lung compliance and lung resistance may be averaged, low-pass filtered or otherwise combined with the previously determined values. These revised values are then stored for use in later delivery of PA ventilation and the ventilator returns to providing PA ventilation to the patient.

Figure 4:
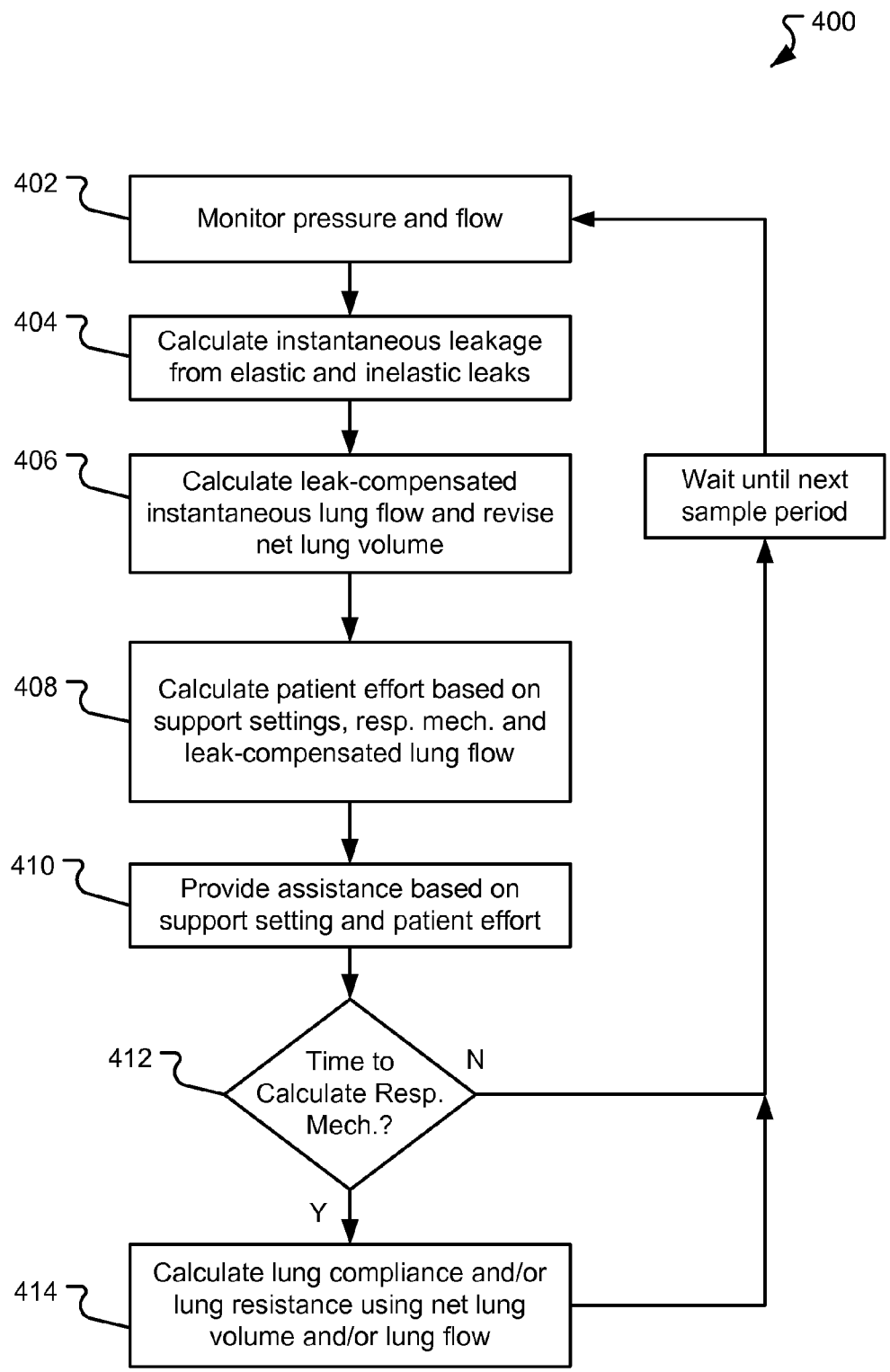
FIG. 4 illustrates an embodiment of a method for providing a leak-compensated PA breath to a patient.

FIG. 4 illustrates an embodiment of a method for providing a leak-compensated PA breath to a patient. In an embodiment, the method 400 corresponds to the operations performed during the PA ventilation operation 306 and the respiratory mechanics maneuver operation 308 discussed with reference to FIG. 3. In the embodiment of the method 400 illustrated, the operations occur repeatedly while the ventilator is providing PA ventilation, such as once a sample period or computation cycle.

During PA ventilation, the pressure and flow and other parameters of the system are monitored, illustrated by the monitoring operation 402. In an embodiment, the monitoring operation 402 collects data including the instantaneous pressure and/or flow at or indicative of one or more locations in the ventilation tubing system. Depending upon how a particular leak model is defined, the operation 402 may also include making one or more calculations using data from pressure and flow measurements taken by the sensors. For example, a model may require a flow measurement as observed at the patient interface even though the ventilation system may not have a flow sensor at that location in the ventilation tubing system. Thus, a measurement from a sensor or sensors located elsewhere in the system (or data from a different type of sensor at the location) may be mathematically manipulated in order to obtain an estimate of the flow observed at the patient interface in order to calculate the leak using the model.

The data obtained in the monitoring operation 402 is then used to calculate leakage from the ventilator tubing system in a leakage calculation operation 404. In an embodiment, the leakage calculation operation 404 uses the data obtained in the monitoring operation 402, e.g., some or all of the instantaneous pressure and flow data collected during the monitoring operation 402 as well as information about the current respiratory phase (inhalation or exhalation).

The leakage calculation operation 404 calculates an instantaneous leakage flow or volume for the sample period. The instantaneous leakage is calculated using a mathematical formula that has been previously determined. Any leakage model, now known or later developed, may be used. In an embodiment, the mathematical formula is a leakage model that separates the leak into the sum of two leak components, inelastic leak and elastic leak, in which each component represents a different relationship between the quantity of leakage from the ventilation system and the measured current/instantaneous pressure and/or flow of gas in the ventilation system. As discussed above, the inelastic leak may be modeled as the flow through a rigid orifice of a fixed size while the elastic leak may be modeled as the flow through a different orifice of a size that changes based on the pressure (or flow) of the gas in the ventilation system.

An example of a method and system for modeling leak in a ventilation system as a combination of an elastic leak component and an inelastic leak component can be found in commonly-assigned U.S. Provisional Patent Application Ser. No. 61/041,070, filed Mar. 31, 2008, titled VENTILATOR LEAK COMPENSATION, which application is hereby incorporated by reference herein. The VENTILATOR LEAK COMPENSATION represents one way of characterizing the leak from a ventilation system as a combination of elastic and inelastic components. Other methods and models are also possible and may be adapted for use with this technology.

The mathematical formula used to calculate leakage may contain several parameters that are empirically determined and that may be periodically or occasionally revised in order to maintain the accuracy of the leakage estimate. For example, in an embodiment the parameters of a leakage formula include a first constant associated with the rigid orifice and a second constant associated with the variable-sized orifice. At various times during ventilation, the calculated leakage may be checked against a measured leakage and, if the estimate is significantly different from the measured leakage, the constants may be revised. This revision of the parameters in a leakage formula may be done as part of the leakage calculation operation 404 or may be done as a separate operation (not shown) that may, or may not, be performed every sample period.

The term instantaneous is used herein to describe a determination made for any particular instant or sampling period based on the measured data for that instant. For example, if a pressure measurement is taken every 5 milliseconds (sample period), the pressure measurement and the leakage model can be used to determine an instantaneous leak flow based on the instantaneous pressure measurement. With knowledge of the length of the sample period, the instantaneous flow may then be used to determine an instantaneous volume of gas leaking out of the circuit during that sample period. For longer periods covering multiple sample periods the instantaneous values for each sample period may be summed to obtain a total leakage volume. If a measurement is also the most recent measurement taken, then the instantaneous value may also be referred to as the current value.

After the current leak has been calculated, the method 400 further estimates the leak-compensated instantaneous lung flow to or from the patient in a lung flow estimation operation 406. The estimated lung flow is compensated for the leak flow calculated in the instantaneous leak calculation operation 404 so that it represents a more accurate estimate of the actual flow into (or out of depending on the point of view and period selected) the lungs of the patient.

In the embodiment illustrated, the leak-compensated net lung volume is also calculated as part of the lung flow estimation operation 406. In an embodiment, this may be performed by maintaining a running summation of net flow into/out of the lung over the period of a breath. For example, upon triggering inhalation, the ventilator may set a variable corresponding to net lung volume to zero and, each sample period, update this net lung volume to include the detected leak-compensated instantaneous lung flow delivered to the patient during that sample period.

In the PA ventilation method 400 illustrated, the leak-compensated lung flow or net volume is then used along with the support setting and the previously determined lung resistance and lung compliance (which were themselves determined using leak-compensated lung flows and net lung volumes) to calculate the amount of assistance to provide during ventilation.

The PA ventilation method 400 also includes calculating the patient effort in effort calculation operation 408. As described above, the operation 408 may use one or more equations that relate the amount of pressure to calculate the patient's effort based on the instantaneous lung flow, current lung volume, lung compliance, lung resistance, support setting and other factors such as circuit compliance and resistance. Various methods are known in the art for calculating patient effort that use one or more respiratory mechanics and other parameters measurable while providing ventilatory support. Any such method for determining patient effort, now known or later developed, may be used herein.

The appropriate amount of ventilation is then provided in a ventilation operation 410. In this operation, the patient effort calculated above and the support setting are used to determine how much assistance to provide. Of course, if there is no patient effort (i.e., during the expiratory phase), no ventilation is provided. In this case, the appropriate ventilation may be providing a predetermined positive end expiratory pressure (PEEP) level. Depending on the equations used, the effort calculation operation 408 may not be technically necessary as the amount of ventilation to provide may be determined directly from the monitored data and the previously determined values of lung compliance and resistance using an appropriate algorithm.

The PA ventilation method 400 also periodically determines the respiratory mechanics from the leak-compensated lung parameters, which is illustrated by the determination operation 412. For example, in an embodiment respiratory mechanics may be calculated on a fixed or random schedule or calculated in response to an explicit operator command. In addition, depending on the respiratory mechanics determination method used, there may be a requirement that the respiratory mechanics calculation (using data collected during the breath) be performed at a certain point within the patient's respiration such as at the end of the inspiratory phase or the end of the expiratory phase or after the completion of a specific maneuver (e.g., an Inspiratory Hold Maneuver). The respiratory mechanics calculation includes the performance a respiratory mechanics "maneuver," that is a specified set of controlled actions on the part of the ventilator. In an embodiment, the maneuver includes interrupting the therapeutic delivery of respiratory gas for a period of time and monitoring and/or changing the pressure and flow, so that data concerning the response of the patient's lung to the controlled actions may be obtained. An example of a respiratory mechanics maneuver is provided below with reference to the static determination of lung compliance.

If it is time to calculate respiratory mechanics, a calculate respiratory mechanics operation 414 is performed. The calculate respiratory mechanics operation 414 may also include performing the appropriate maneuver, as necessary to obtain the data for the respiratory mechanics model being used. In the operation 414, the necessary data for the respiratory mechanics model being used is obtained and the respiratory mechanics parameters are estimated.

In the calculate respiratory mechanics operation 414 leak-compensated values are used to estimate the respiratory mechanics. For example, if the respiratory mechanics model being used requires a total delivered lung volume, the leak-compensated lung volume is used. Likewise, if an instantaneous lung flow is required, a leak-compensated instantaneous lung flow is used in generating the estimate.

The method 400 is then repeated every computational cycle or sample period, as illustrated by the feedback loop, so that the instantaneous lung flow and net lung flow are continuously determined and, when appropriate, the respiratory mechanics are recalculated based on the current leak-compensated data. In an alternative embodiment, the leak-compensation of lung flow and net delivered lung volume may be performed as part of the calculate respiratory mechanics operation 414 in order to reduce the number of calculations a processor must perform every cycle.

The following is a discussion of two embodiments of methods for compensating the estimation of respiratory mechanics in the presence of leaks. The first embodiment is that of applying leak compensation to a static compliance and resistance determination. The second embodiment is that of applying leak compensation to a dynamic compliance determination.

Leak-Compensation of Static Determination of Lung Compliance

Figure 5:
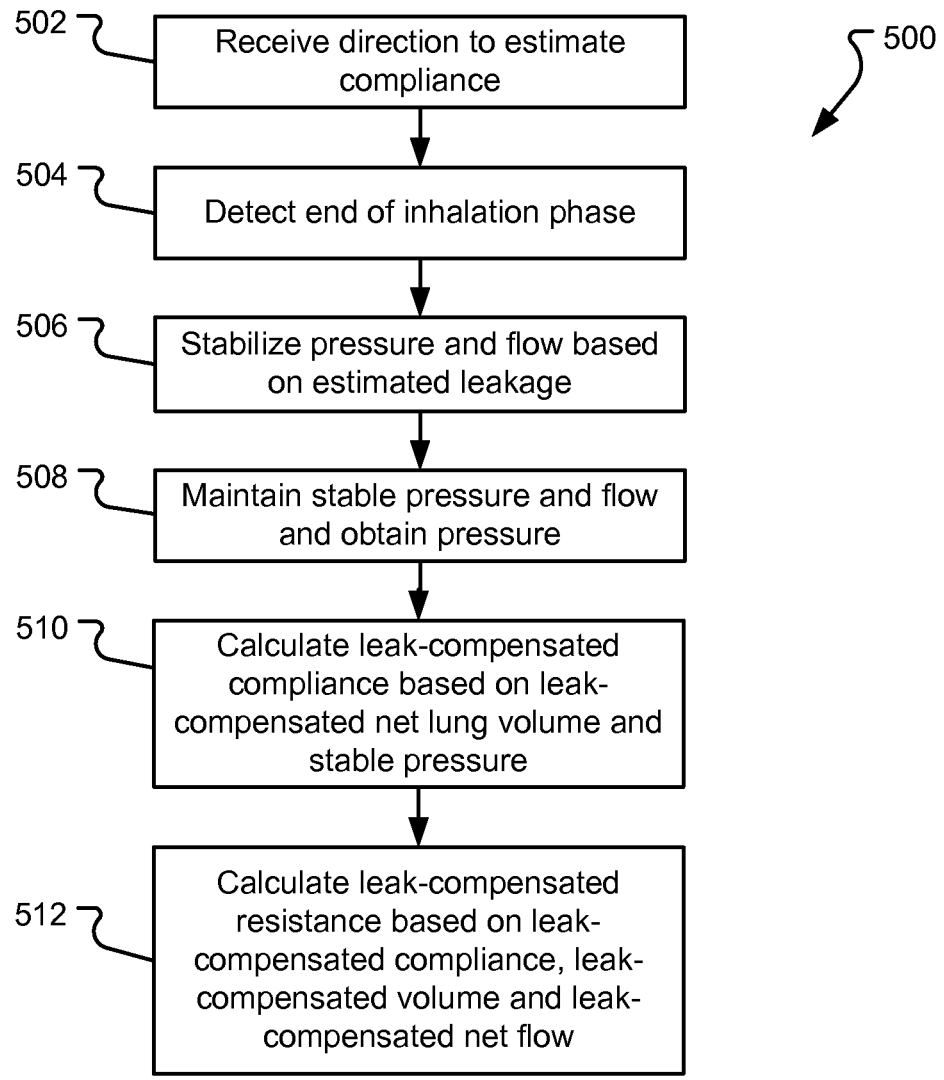
FIG. 5 illustrates an embodiment of a method for estimating respiratory mechanics of patient that utilizes a respiratory mechanics maneuver.

FIG. 5 illustrates an embodiment of a method for estimating respiratory mechanics of patient that utilizes a respiratory mechanics maneuver. In the embodiment shown, the ventilator is providing respiratory gas to a patient in accordance with some mode of operation such as a mandatory mode or a pressure assist mode (e.g., a mandatory volume-controlled (VCV) inspiration under square waveform setting or a mandatory pressure-controlled (PCV) inspiration with specific settings, or execute an inspiratory hold at the end of a PA inspiration), as is well known in the art. During operation, an operator command to estimate the compliance of the patient is received in a receive command operation 502. In an embodiment, the command may be entered by the operator of the ventilator via selection of a button or other interface element on a user interface of the ventilator. In an alternative embodiment, the ventilator may perform the method 500 automatically such as periodically, randomly or upon the detection of predetermined respiratory event.

In the embodiment shown, the system performs a respiratory maneuver which includes the forced imposition of a stable period at the end of an inspiratory phase so that there is no flow delivery to or from the patient's lung. The method 500 includes a delay until the next end of an inspiratory phase is detected, as illustrated by detect end of inspiratory phase operation 504.

When the end of the inspiratory phase is detected, a stabilization operation 506 is performed. In an embodiment, the operation 506 includes stabilizing the pressure and flow in the patient circuit so that there is no flow into or out of the patient's lungs at the point in which the lungs have taken a breath and thus are expanded with a known volume of gas (as determined during normal operation of the ventilator as discussed above with reference to the leak-compensated lung volume).

The stabilization operation 506 and the maintain stable condition operation 508 (discussed below) may sometimes be referred to collectively as a pause maneuver or a plateau maneuver. They are separated in this discussion for clarity purposes.

In order to stabilize the pressure and flow to achieve no flow between the circuit and the patient, if there are leaks in the tubing system these leaks are compensated for by the ventilator. Thus, in order to stabilize the flow the ventilator provides a leak-compensation flow that is equal to the amount of leakage from the system estimated by the leakage model at the stable pressure.

In practice, the stabilization of the pressure and flow is an iterative process in which the ventilator monitors the pressure and adjusts delivered flow until the pressure and flow stabilize at the point where the pressure and flow correspond to a solution to the leak model and the lung flow is practically zero, i.e., the current flow provided by the ventilator is the leakage flow determined from the model using the current pressure. In an embodiment, for a flow and pressure to be considered stable, a certain acceptable error may be allowed between the calculated leakage (calculated based on the current pressure) and the actual measured flow. Such an error may be predetermined amount or range based on an absolute difference between delivery and calculated flow or pressure or relative difference (e.g., calculated flow within x % of actual stable flow at a given pressure). Various methods for stabilizing pressure and flow in a ventilation tubing system are known in the art and any suitable method may be adapted for use in conjunction with the technology described in this disclosure.

When attempting to stabilize the pressure and flow during the stabilization operation 506, the leakage model may be used to increase the speed of the stabilization through a prediction of the likely resulting leakage flow at different pressures. This information may be used to determine a more accurate initial starting point for the stabilization and determine more accurate selection of adjustments to be made in order to more quickly converge on the stable pressure and flow.

After a stable pressure has been achieved, in the embodiment shown a maintain stable condition operation 508 is performed. The maintain stable condition operation 508 may maintain the stable pressure and stable, leak-compensating flow for a predetermined period of time such as 25-200 milliseconds or more preferably between 50-100 milliseconds. During the operation 458, the drop in pressure over the period of the maneuver may be monitored to ensure that it is within some acceptable performance threshold. If it is not, the ventilator may resume attempting to stabilize the pressure and flow or may abort the method and attempt the method 500 at the end of the next inspiratory phase.

The stable pressure observed during the maintain stable condition operation 508 is then used to calculate the leak-compensated compliance in a lung compliance calculation operation 510. The pressure value used may be an actual pressure or an average pressure observed over the maneuver period. Alternatively, different values derived from or based on the observed stable pressure may be calculated and used depending on the data required by the particular respiratory mechanics model being utilized.

In addition to using the stable pressure obtained during the pause maneuver, the compliance calculation operation 510 further utilizes leak-compensated lung flow and leak-compensated net lung volume when performing the calculation.

As discussed above, any suitable model for calculating lung compliance may be used. For example, in an embodiment of the compliance calculation operation 510 compliance is calculated using the following simple model:

Stable pressure=Leak-Compensated Net Lung Volume/Compliance, or, stated a different way, Compliance=Leak-Compensated Net Lung Volume/Stable pressure.

By using a leak-compensated value for lung volume and a stable pressure determined while compensating for leaks in the patient circuit, a more accurate leak-compensated lung compliance is estimated.

The leak-compensated compliance then may be used in a subsequent operation to determine a leak-compensated lung resistance. In the embodiment of the method 500 shown, this is illustrated by optional resistance calculation operation 512. In an embodiment of the resistance calculation operation 512 after the leak-compensated compliance has been determined, a resistance model that calculates lung resistance based on pressure, flow and compliance may be used to calculate resistance. An example of one such resistance model is as follows:

$$P(t_2)-P(t_1)=(V(t_2)-V(t_1))/C+R^*(Q(t_2)-Q(t_1))$$

In which $t_1$ and $t_2$ are different times during a breath, P(t) is the airway pressure at time t, V(t) is the delivered lung volume at time t, C is the lung compliance, R is the lung resistance and Q(t) is the net lung flow at time t. In the resistance model provided above, leak-compensated lung flow, leak-compensated net lung volume and leak-compensated lung compliance are utilized to obtain a leak-compensated resistance. This computation may be performed repeatedly over several appropriate time windows and combined together (e.g., by an averaging method) to generate an estimate for lung resistance. Also, lung resistance may be determined from the leak-compensated exhalation flow waveform subsequent to the inspiratory pause maneuver using algorithms for resistance estimation under no leak conditions.

In an alternative embodiment of method 500, if it is determined that the ventilator has relatively low leakage, the lung compliance calculation operation 510 may forego the use of leak-compensated lung flow and net lung volume but still utilize the stable pressure determined through the provision of a leak-compensating flow during the pause maneuver. Lung compliance calculated in this fashion is still considered leak-compensated as the stable pressure was determined by compensating for leakage during the pause maneuver when generating the stable pressure.

Leak-Compensation of Dynamic Determination of Luna Compliance and Resistance

Figure 6:
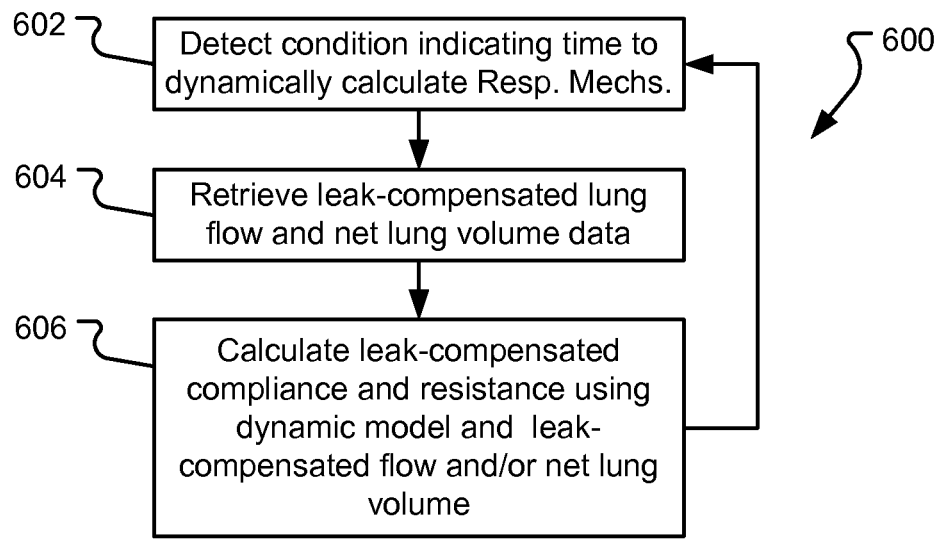
FIG. 6 illustrates an embodiment of a method for dynamically estimating respiratory mechanics of patient.

FIG. 6 illustrates an embodiment of a method for dynamically estimating respiratory mechanics of patient. This may be used as an alternative method of calculating lung compliance and resistance, thereby obviating the need to perform respiratory maneuvers during PA ventilation.

In the embodiment shown, the ventilator is providing respiratory gas to a patient in accordance with some mode of operation such as a mandatory mode or a pressure assist or support or PA mode, as is well known in the art. During operation, the ventilator detects a condition that indicates that it is time to estimate the respiratory mechanics of the patient. This is illustrated by the detection operation 602. In an embodiment, the condition detected may be a command entered by the operator of the ventilator via selection of a button or other interface element on a user interface of the ventilator. Alternatively, the ventilator may perform the dynamic estimation automatically such as during every breath, after a predetermined period of time or after the detection of some occurrence such as once every 100 breaths or upon detection of certain flow conditions.

Following determination that it is time to calculate the dynamic respiratory mechanics, the method 600 retrieves and/or calculates leak-compensated lung flow and leak-compensated net lung volume as necessary depending on whether the leak-compensated data already exists or not. For example, in an embodiment the leak-compensated lung flows for each sampling period may be available but the leak-compensated net lung volume may only be available "as needed" by calculating it from the compensated lung flow data.

The method 600 then calculates the leak-compensated respiratory mechanics in a calculation operation 606. The leak-compensated respiratory mechanics are calculated from a predetermined dynamic respiratory mechanics model using the leak-compensated lung flows, leak-compensated net lung volume(s) and pressure in order to obtain estimates of dynamic compliance and dynamic resistance that are compensated for the leaks in the tubing system. The method 600 is then repeated as necessary.

Any respiratory mechanics model may be used as long as the model may be adapted to be used in a dynamic calculation, that is without interrupting the ventilation of the patient. Many such models are known in the art, some requiring iterative solutions of a set of multiple equations using data obtained over of a period of time.

Figure 7:
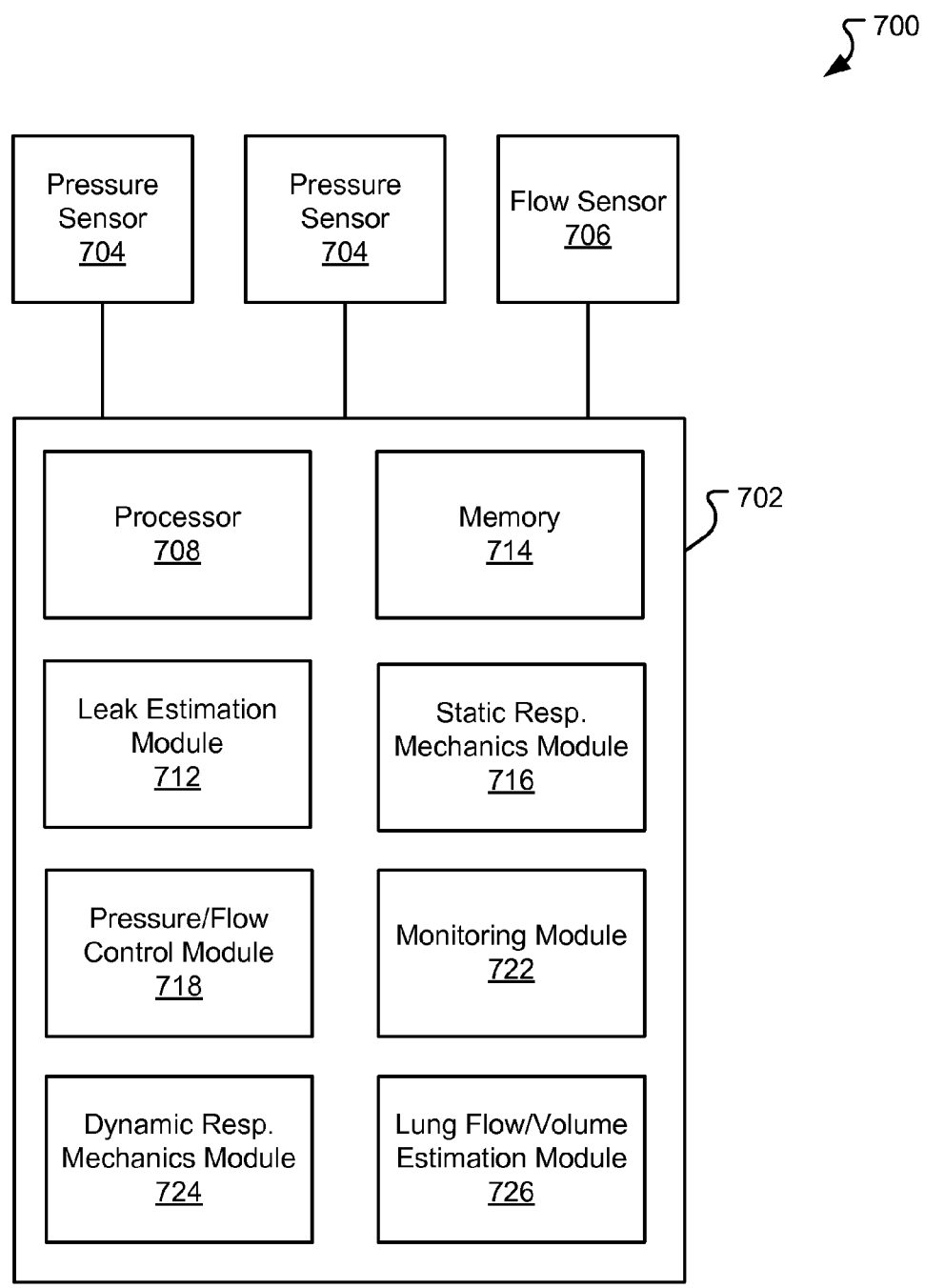
FIG. 7 illustrates a functional block diagram of modules and other components that may be used in an embodiment of ventilator that compensates for elastic and rigid orifice sources of leaks when performing PA ventilation.

FIG. 7 illustrates a functional block diagram of modules and other components that may be used in an embodiment of ventilator that compensates for elastic and rigid orifice sources of leaks when determining patient respiratory mechanics. In the embodiment shown, the ventilator 700 includes pressure sensors 706 (two are shown placed at different locations in the system), flow sensors (one is shown), and a ventilator control system 702. The ventilator control system 702 controls the operation of the ventilator and includes a plurality of modules described by their function. In the embodiment shown, the ventilator control system 702 includes a processor 708, memory 714 which may include mass storage as described above, a leak estimation module 712 incorporating a parametric leak model accounting for both elastic and rigid orifice leak sources such as that described in U.S. Provisional Application 61/041,070 previously incorporated herein, a leak-compensated static respiratory mechanics module 716, a pressure and flow control module 718, a monitoring module 722, a leak model module 720, a leak-compensated dynamic respiratory mechanics module 724, and a leak-compensated lung flow and volume estimation module 726. The processor 708 and memory 716 have been discussed above. Each of the other modules will be discussed in turn below.

The main functions of the ventilator such as receiving and interpreting operator inputs and providing therapy via changing pressure and flow of gas in the ventilator circuit are performed by the control module 718. In the context of the methods and systems described herein, the module 718 will perform one or more actions upon the determination that a patient receiving therapy is inhaling or exhaling.

In the embodiment described herein, the control module 718 determines and provides the appropriate amount of ventilation when in PA ventilation mode. This may include calculating patient effort and, based on the patient effort and the support setting, determining the appropriate amount of ventilation, i.e., the pressure and/or flow to provide to the patient. This may include performing one or more calculations based on leak-compensated lung flow, leak-compensated lung volume, leak-compensated lung compliance and leak-compensated lung resistance. PA ventilation is based on an estimation of patient's respiratory effort, therefore, patient effort may be first calculated and then the amount of ventilation (desired pressure reference) calculated therefrom.

The static calculation of respiratory mechanics is performed by the leak-compensated static respiratory mechanics module 716. The module 716 utilizes one or more respiratory models suitable for static determination of respiratory mechanics and one or more embodiments of the method 400 described above to calculate leak-compensated respiratory mechanics such as lung compliance and lung resistance. The module 716 uses leak-compensated values for one or both of lung flows and net lung volume. Leak-compensated values may be retrieved if they have already been calculated or may be calculated as needed from leakage information received from the leak-compensated lung flow and net lung volume estimation module 726. When calculating static respiratory mechanics, the module 716 may control the operation of the ventilator so that a pause maneuver is performed when required. Alternatively, some or all of the actions required in a pause maneuver may be controlled by the control module 718 in response to a respiratory mechanics calculation request and the data obtained during the maneuver provided to the static respiratory mechanics module 716.

The dynamic calculation of respiratory mechanics is performed by the leak-compensated dynamic respiratory mechanics module 724. The module 724 utilizes one or more dynamic respiratory models and one or more embodiments of the method 500 described above to calculate leak-compensated respiratory mechanics such as lung compliance and lung resistance. The module 724 uses leak-compensated values for one or both of lung flows and net lung volume. Leak-compensated values may be retrieved if they have already been calculated or may be calculated from leakage information received from the leak-compensated lung flow and net lung volume estimation module 726.

The current conditions in the ventilation system are monitored by the monitoring module 722. This module 722 collects the data generated by the sensors 704, 706 and may also perform certain calculations on the data to make the data more readily usable by other modules or may process the current data and or previously acquired data or operator input to derive auxiliary parameters or attributes of interest. In an embodiment, the monitoring module 722 receives data and provides it to each of the other modules in the ventilator control system 702 that need the current pressure or flow data for the system.

In the embodiment shown, compensated lung flows are calculated by the lung flow module 726. The lung flow module 726 uses a quantitative model for lung flow of the patient during both inhalation and exhalation and from this characterization and pressure and flow measurements generates an estimate for instantaneous lung flow. In an embodiment, lung flow may be simply determined based on subtracting the estimated leak flow and measured outflow via the expiratory limb from the flow into the inspiratory limb, thereby generating a leak-compensated net flow into (or out of) the lung. The lung flow module 726 may or may not also calculate an ongoing leak-compensated net lung volume during a patient's breath as described above. Compression in the circuits and accessories may also be accounted for to improve the accuracy of estimated lung flow.

The leak model parameters are generated by the leak estimation module 712 which creates one or more quantitative mathematical models, equations or correlations that uses pressure and flow observed in the ventilation system over regular periods of respiratory cycles (inhalation and exhalation) and apply physical and mathematical principles derived from mass balance and characteristic waveform settings of ventilation modalities (regulated pressure or flow trajectories) to derive the parameters of the leak model incorporating both rigid and elastic (variable pressure-dependent) orifices. In an embodiment, the mathematical model may be a model such as:

$$Q_{inelastic} = R_1 * P_i^x$$

$$Q_{elastic} = R_2 * P_i^y$$

wherein $Q_{elastic}$ is the instantaneous leak flow due to elastic leaks in the ventilation system, $Q_{inelastic}$ is the instantaneous leak flow due to inelastic leaks in the ventilation system, $R_1$ is the inelastic leak constant, $R_2$ is the elastic leak constant, $P_i$ is the current or instantaneous pressure measurement, x is an exponent for use when determining the inelastic leak and y is an exponent different than x for use when determining the elastic leak. The group $R_1*P_i^x$ represents flow through an orifice of fixed size as a function of instantaneous pressure $P_i$ and the group $R_2*P_i^y$ represents flow through a different orifice that varies in size based on the instantaneous pressure. The equations above presuppose that there will always be an elastic component and an inelastic component of leakage from the ventilation system. In the absence of an elastic component or a leak source of varying size, $R_2$ would turn out be zero.

In the embodiment shown, the current or instantaneous elastic leak is calculated by the leak estimation module 712. The calculation is made using the elastic leak portion of the leak model developed by the leak estimation module 712 and the pressure data obtained by the monitoring module 722. The leak estimation module 712 may calculate a new instantaneous elastic leak flow or volume for each pressure sample taken (i.e., for each sampling period) by the monitoring module 722. The calculated elastic leak may then be provided to any other module as needed.

In the embodiment shown, the current or instantaneous inelastic leak is also calculated by the leak estimation module 712. The calculation is made using the inelastic leak portion of the leak model and the pressure data obtained by the monitoring module 722. The leak estimation module 712 may calculate a new instantaneous inelastic leak flow or volume for each pressure sample taken (i.e., for each sampling period) by the monitoring module 722. The calculated inelastic leak may then be provided to any other module as needed.

The system 700 illustrated will compensate lung flow for leaks due to elastic and inelastic leaks in the ventilation system. Furthermore, the system may perform a dynamic compensation of lung flow based on the changing leak conditions of the ventilation system and the instantaneous pressure and flow measurements. The system then compensates the respiratory mechanics calculations based on the estimated leakage in the system. By compensating for the inelastic as well as the elastic components of dynamic leaks, the medical ventilator can more accurately and precisely estimate the respiratory mechanics of a patient including estimating the lung compliance and lung resistance.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. For example, the operations and steps of the embodiments of methods described herein may be combined or the sequence of the operations may be changed while still achieving the goals of the technology. In addition, specific functions and/or actions may also be allocated in such as a way as to be performed by a different module or method step without deviating from the overall disclosure. In other words, functional elements being performed by a single or multiple components, in various combinations of hardware and software, and individual functions can be distributed among software applications. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the technology described herein. For example, the systems and methods described herein could be adapted to automatically determine leak-compensated resistance and/or compliance and initiate an alarm if the leak-compensated values are outside of a specified range for predetermined leakage values, thus eliminating false resistance and compliance alarms due to changes in leakage. Numerous other changes may be made which will readily suggest themselves to those skilled in the art and which are encompassed in the spirit of the disclosure and as defined in the appended claims.

What is claimed is:

1. A pressure support system comprising:
   a pressure generating system adapted to generate a flow of breathing gas;
   a ventilation tubing system including a patient interface device for connecting the pressure generating system to a patient;
   one or more sensors operatively coupled to the pressure generating system or the ventilation tubing system, each sensor capable of generating an output indicative of a pressure of the breathing gas;
   a leak estimation module that identifies leakage in the ventilation tubing system;
   a respiratory mechanics calculation module that generates a leak-compensated lung compliance and a leak-compensated lung resistance based on the leakage and at least one output indicative of a pressure of the breathing gas; and
   a proportional assistance ventilation module that causes the pressure generating system to provide ventilation to the patient based on patient effort and a support setting, wherein the patient effort is determined from the leakage, the leak-compensated lung compliance and the leak-compensated lung resistance.

2. The system of claim 1 wherein the respiratory mechanics module is a static respiratory mechanics module that uses a static respiratory mechanics model to determine a leak-compensated static lung compliance and a leak-compensated static lung resistance based on a leak-compensated lung flow and an output of at least one sensor.

3. The system of claim 1 wherein the respiratory mechanics module is a dynamic respiratory mechanics module that uses a dynamic respiratory mechanics model to determine at least one of a leak-compensated dynamic lung compliance and a leak-compensated dynamic lung resistance based on the leak-compensated lung flow and an output of at least one sensor.

4. The system of claim 1 wherein the leak estimation module further identifies an inelastic leakage in the ventilation tubing system and wherein the compensation module further generates the leak-compensated lung flow based on the inelastic leakage.

5. The system of claim 4 further comprising:
   a pressure monitoring module that monitors at least one output of the one or more sensors and provides data indicative of the pressure of the breathing gas to the leak estimation module.

6. A controller for a medical ventilator comprising:
   a microprocessor;
   a module that compensates calculations of lung compliance and lung resistance based on an instantaneous elastic leakage of breathing gas from a variable orifice and an instantaneous inelastic leakage of breathing gas from a fixed orifice of a ventilation tubing system; and
   a pressure generating module controlled by the microprocessor that provides proportional assist ventilation based on the compensated lung compliance and lung resistance.

7. The controller of claim 6 further comprising:
   a leak estimation module that identifies the instantaneous inelastic leakage from the associated ventilation tubing system and the instantaneous elastic leakage from the associated ventilation tubing system.

* * * * *